US006915168B1

(12) United States Patent
Benz et al.

(10) Patent No.: US 6,915,168 B1
(45) Date of Patent: Jul. 5, 2005

(54) MEDICAL DEVICES CONTAINING SEGMENTED POLYURETHANE BIOMATERIALS

(76) Inventors: Michael D. Benz, 15410 Hematite St. Northwest, Ramsey, MN (US) 55303; Kelvin Bonnema, 128 75th Ave. North, Brooklyn Park, MN (US) 55444; Edward Didomenico, 633 School St., Anoka, MN (US) 55303; Christopher M. Hobot, 40 Pleasant La. West, Tonka Bay, MN (US) 55331; David L. Miller, 154 Glenview Ave., Circle Pines, MN (US) 55014

( * ) Notice: Subject to any disclaimer, the term of this patent is extended or adjusted under 35 U.S.C. 154(b) by 0 days.

(21) Appl. No.: 09/423,332
(22) PCT Filed: May 8, 1998
(86) PCT No.: PCT/US98/09381

§ 371 (c)(1),
(2), (4) Date: Nov. 4, 1999

(87) PCT Pub. No.: WO98/50086

PCT Pub. Date: Nov. 12, 1998

Related U.S. Application Data
(60) Provisional application No. 60/046,856, filed on May 8, 1997.

(51) Int. Cl.[7] .............................. A61N 1/05; A61N 1/02
(52) U.S. Cl. ............................ 607/122; 525/86; 525/92
(58) Field of Search ............................ 607/122; 525/46, 525/92; 528/44, 72

(56) References Cited

U.S. PATENT DOCUMENTS

| 4,426,494 A | * | 1/1984 | Beasley et al. ............... 525/86 |
| 4,675,361 A | * | 6/1987 | Ward, Jr. ..................... 525/92 |
| 4,873,308 A | | 10/1989 | Coury et al. |
| 5,040,544 A | | 8/1991 | Lessar et al. |
| 5,238,006 A | | 8/1993 | Markowitz |
| 5,375,609 A | | 12/1994 | Molacek et al. |
| 5,480,421 A | | 1/1996 | Otten |
| 5,589,563 A | * | 12/1996 | Ward et al. ................... 528/44 |
| 6,111,052 A | * | 8/2000 | DiDomenico et al. ........ 528/72 |

FOREIGN PATENT DOCUMENTS

EP         94302893        11/1994

OTHER PUBLICATIONS

Brandwood et al, "Polyurethane Elastomers Containing Novel Macrodiols II. In Vivo Evaluation", *Fourth World Biomaterials Congress*; Apr. 24–28, 1992; Berlin, Federal Republic of Germany; p. 201.

Byrne et al, "Hydroxy Terminated Polyethylene and Polyurethanes Prepared From it", Polymer Research Branch, SLcMT–EMP; Army Materials Technology Laboratory; Watertown, MA, pp 657–658.

Byrne et al, "Polyethylene–Based Polyurethane Copolymers and Block Copolymers", Army Research Laboratory, Report No. ARL–TR 649; Watertown, MA (Nov. 1994) pp 1–31.

Byrne et al, "Polyethylene–Based Polyurethane Copolymers and Block Copolymers", *Macromol.Symp.*, 91, 1–26 (1995).

(Continued)

*Primary Examiner*—Carl Layno

(57) ABSTRACT

In one aspect, the present invention relates to a medical device, such as a medical electrical lead, comprising a biomaterial formed from a polymer comprising urethane groups and saturated linear polyethylene moieties wherein the saturated linear polethylene moieties have greater than 12 carbon atoms per moiety. In another aspect, the present invention relates medical devices comprising a biomaterial formed from segmented polymers or polymers having an elongation of greater than 50%. Exemplified polymers contain compounds of the formula HO—$(CH_2)_n$—OH wherein n is greater than 12.

29 Claims, 6 Drawing Sheets

OTHER PUBLICATIONS

Courey et al, "Biomedical Uses of Polyurethanes", *Advances in Urethane Science and Technology*, 9, 130–168 (1984).

Coury et al, "Factors and Interactions Affecting the Performance of Polyurethane Elastomers in Medical Devices", uJournal of Biomaterials Applications 3, pp. 130–179 (Oct. 1988).

Fraser et al, "Degradable Cyclooctadiene/Acetal Copolymers: Versatile Precursors to 1,4–Hydroxytelechelic Polybutadiene and Hydroxytelechelic Polyethylene," *Macromolecules*, 28, 7256–7261 (1995).

Frisch et al, "Polyurethane Elasstomers Based Upon Novel Hydrocarbon–Based Diols", Polymer Institute, Univ. of Detroit Mercy; Detroit, Michigan, pp 395–416.

Hillmyer et al, "The ROMP of COD by a Well–Defined Metathesis Catalyst in the Presence of a Difunctional Chain Transfer Agent: The Preparation of Hydroxy–Telechelic 1,4–Poly (butadiene),"*Polymer Preprints* 34, 388–389 (1993).

Hillmyer et al, "Chain Transfer in the Ring–Opening Metathesis Polymerization of Cyclooctadiene Using Discrete metal Alkylidenes," *Macromolecules*, 28, 8662–8667 (1995).

Hillmyer et al, "Preparation of Hydroxytelechelic Poly(butadiene) via Ring Opening Methathesis Polymerization Employing a Well–Defined Methathesis Catalyst," *Macromolecules*, 25, 872–874 (1993).

Hillmyer, "The Preparationof Functionalized Polymers by Ring–Opening Metathesis Polymerization", Thesis–California Institute of Technology (1995); Dissertation Services—UMI; Ann Arbor, Michigan; pp. 1–131.

Li et al, "Novel Blood–Compatible Polyurethanes Containing Poly (butadiene) Soft Segments and Phosphatidylcholine Analogues for Biomedical Applications", *Chem.Mater.* 8, 1441–1450 (1996).

Meijs et al, "Polyurethane Elastomers Containing Novel Macrodiols I. Synthesis and Properties", *Fourth World Biomaterials Congress*; Apr. 24–28, 1992; Berlin, Fed. Republic of Germany, p 473.

Ward et al, "Thermoplastic Siloxane–Urethane Block Copolymers and Terpolymers for Biochemical Use"; *Third World Biomaterials Congress*; Apr. 21–25, 1988; Kyoto, Japan; p. 433.

Ward et al, "The Effect of Phase Separation and End Group Chemistry on In Vivo Biostability of Polyurethanes",*ASAIO* (1996), Washington, DC.

Yokelson et al, "New Hydrocarbon–based Diols for Polyurethane Elastomers", *Polyurethanes 95: Proceedings of the Polyurethanes 1995 Conference Sponsored by the SPI Polyurethanes Division*; Sep. 26–29, 1995; Chicago, Ill. pp 100–108.

* cited by examiner

MEDICAL DEVICES CONTAINING SEGMENTED POLYURETHANE BIOMATERIALS

This application claims priority from a provisional patent application filed on May 8, 1997 entitled "Biostable Polyurethanes Which Show Improved Processability" and assigned Provisional Ser. No. 60/046,856, which is incorporated herein by reference.

FIELD OF THE INVENTION

This invention relates to medical devices that include segmented polyurethane biomaterials, particularly elastomers, containing saturated linear polyethylene moieties (typically, hard segments) that provide crystallinity to the polymer.

BACKGROUND OF THE INVENTION

The chemistry of polyurethanes is extensive and well developed. Typically, polyurethanes are made by a process in which a polyisocyanate is reacted with a molecule having at least two hydrogen atoms reactive with the polyisocyanate, such as a polyol. The resulting polymer can be further reacted with a chain extender, such as a diol or diamine, for example. The polyol or polyamine can be a polyester, polyether, or polycarbonate polyol or polyamine, for example.

Polyurethanes can be tailored to produce a range of products from soft and flexible to hard and rigid. They can be extruded, injection molded, compression molded, and solution spun, for example. Thus, polyurethanes are important biomedical polymers, and are used in implantable devices such as artificial hearts, cardiovascular catheters, pacemaker lead insulation, etc.

Commercially available polyurethanes used for implantable applications include BIOSPAN segmented polyurethanes available from Polymer Technology Group of Berkeley, Calif., PELLETHANE segmented polyurethanes available from Dow Chemical, Midland, Mich., and TECOFLEX segmented polyurethanes available from Thermedics, Inc., Woburn, Mass. These polyurethanes and others are described in the article "Biomedical Uses of Polyurethanes," by Coury et al., in *Advances in Urethane Science and Technology*, 9, 130–168, edited by Kurt C. Frisch and Daniel Klempner, Technomic Publishing Co., Lancaster, Pa. (1984). Typically, polyether polyurethanes exhibit more biostability than polyester polyurethanes, and are therefore generally preferred polymers for use in biological applications.

Polyether polyurethane elastomers, such as PELLETHANE 2363-80A (P80A) and 2363-55D (P55D), which are believed to be prepared from polytetramethylene ether glycol (PTMEG) and methylene bis(phenyliisocyanate) (MDI) extended with butanediol (BDO), are widely used for implantable cardiac pacing leads. Pacing leads are insulated wires with electrodes that carry stimuli to tissues and biologic signals back to implanted pulse generators. The use of polyether polyurethane elastomers as insulation on such leads has provided significant advantage over silicone rubber, primarily because of the higher tensile strength and elastic modulus of the polyurethanes.

There is some problem, however, with stress cracking of polyurethanes, particularly polyether polyurethanes. When used in insulation on leads, polyether polyurethanes are susceptible to oxidation in the body, particularly in areas that are under stress. When oxidized, polyether polyurethane elastomers can lose strength and form cracks. This can allow bodily fluids to enter the lead and can compromise the function of the device. It is believed that the ether linkages degrade, perhaps due to metal ion catalyzed oxidative attack at stress points in the material.

One approach to solving this problem has been to coat the conductive wire of the lead. Another approach has been to add an antioxidant to the polyurethane. Antioxidants, however, are sacrificial and eventually can be consumed and leave the polymer unprotected. Yet another approach has been to develop new polyurethanes that are more resistant to oxidative attack. Such polyurethanes include only segments that are resistant to metal induced oxidation, such as hydrocarbon- and carbonate-containing segments. For example, polyurethanes that are substantially free of ether and ester linkages have been developed. This includes the segmented aliphatic polyurethanes of U.S. Pat. No. 4,873,308 (Coury et al.), as well as others disclosed in some of the documents listed below in Table 1. Although such materials produce more stable implantable devices than polyether polyurethanes, there is still a need for polymers, particularly polyurethanes suitable for use as insulation on pacing leads.

The use of polyurethanes in medical devices, however, requires attaining not only desirable stability to oxidation and hydrolysis, and desirable physical properties, but also good processability. Oxidation and/or hydrolysis reactions typically lower molecular weights and diminish the elastomeric properties of polyurethanes. Hydrolytic instability can result from the reaction of water with groups, such as ester, carbonate, amide, imide, and urethane groups that form linkages within the backbone of the elastomer. Some of these groups are more resistant than others, but they all can be hydrolyzed. Oxidative instability results from the reaction of activated singlet oxygen and/or molecular oxygen. Singlet oxygen can react with generally stable chemical moieties such as olefins, and atomic oxygen can react with activated chemical moieties on the elastomer backbone, such as carbon radicals. Polymers that contain groups such as ethers, amides, urethanes, unsaturated carbon groups such as olefins and vinyl groups, and groups containing tertiary carbon atoms are susceptible to oxidation.

Processability is more than the ability to melt process a polymer into some desired geometry. It is the inherent ability of the polymer to develop stable properties after being quenched from the melt. In particular, for segmented polyurethane elastomers, it is the ability of the hard segments of a segmented polymer to crystallize, and preferably phase separate, from the soft segments. The extent and rate at which this happens controls the time it takes to get a part out of a mold, the amount of surface tack a part has, and the geometric stability a part has upon exposure to subsequent processing steps.

Typically, processing additives, such as waxes, are added to reduce surface blocking. Generally, these additives bloom to the surface and cause problems with adhesion. To promote release from an injection mold, surfactants (e.g., soaps) and mold release agents are sprayed onto the mold surface. This helps reduce the adhesion at the interface between the mold and the polymer. The ability of molded parts to retain their geometry while being ejected out of the mold is controlled either by adding additives, which help to promote crystallinity, by increasing cycle time to allow the part to cool and set up before being ejected, or by injecting the elastomer at a lower temperature. This latter technique usually results in greater stress development within the part. The ability of the part to withstand subsequent manufacturing processes is typically controlled by annealing the part.

This is done by exposing the part to an elevated temperature (e.g., above the Tg and below the Tm of the polymer) for an extended period of time. It would be desirable to reduce or eliminate processing additives and/or manufacturing steps.

Thus, the identification of materials, particularly polyurethanes, that have the desired stability to oxidation and hydrolysis, and desirable physical properties, as well as good processability, are still needed, particularly for use in implantable medical devices.

TABLE 1a

U.S. Pat. Nos.

| | |
|---|---|
| 4,234,714 | Earing et al. |
| 4,873,308 | Coury et al. |

TABLE 1b

Non-U.S. Patent Documents

| | |
|---|---|
| EP 0 624 612 A1 | Becton Dickinson & Co. |

TABLE 1c

Nonpatent Documents

Brandwood et al., "Polyurethane Elastomers Containing Novel Macrodiols II. In Vivo Evaluation", Fourth World Biomaterials Congress; April 24–28, 1992; Berlin, Federal Republic of Germany; pp. 201.
Byrne et al., "Hydroxy Terminated Polyethylene and Polyurethanes Prepared Form it", Polymer Research Branch, SLCMT-EMP; Army Materials Technology Laboratory; Watertown, MA; pp. 657–658.
Byrne et al., "Polyethylene-Based Polyurethane Copolymers and Block Copolymers", Army Research Laboratory, Report No. ARL-TR-649; Watertown, MA (November 1994) pp. 1–31.
Byrne et al., "Polyethylene-Based Polyurethane Copolymers and Block Copolymers", Macromol. Symp., 91, 1–26 (1995).
Coury et al., "Biomedical Uses of Polyurethanes", Advances in Urethane Science and Technology, 9, 130–168 (1984).
Coury et al., "Factors and Interactions Affecting the Performance of Polyurethane Elastomers in Medical Devices", Journal of Biomaterials Applications, 3, pp. 130–179 (Oct. 1988).
Fraser et al., "Degradable Cyclooctadiene/Acetal Copolymers: Versatile Precursors to 1,4-Hydroxytelechelic Polybutadiene and Hydroxytelechelic Polyethylene," Macromolecules, 28, 7256–7261 (1995).
Frisch et al., "Polyurethane Elastomers Based Upon Novel Hydrocarbon-Based Diols", Polymer Institute, University of Detroit Mercy; Detroit, Michigan, pp. 395–416.
Hillmyer et al., "The ROMP of COD by a Well-Defined Metathesis Catalyst in the Presence of a Difunctional Chain Transfer Agent: The Preparation of Hydroxy-Telechelic 1,4-Poly(butadiene)," Polymer Preprints, 34, 388–389 (1993).
Hillmyer et al., "Chain Transfer in the Ring-Opening Metathesis Polymerization of Cyclooctadiene Using Discrete Metal Alkylidenes," Macromolecules, 28, 8662–8667 (1995).
Hillmyer et al., "Preparation of Hydroxytelechelic Poly(butadiene) via Ring Opening Methathesis Polymerization Employing a Well-Defined Methathesis Catalyst," Macromolecules, 25, 872–874 (1993).
Hillmyer, "The Preparation of Functionalized Polymers by Ring-Opening Metathesis Polymerization", Thesis - California Institute of Technology (1995); Dissertation Services - UMI; Ann Arbor, Michigan; pp. 1–131.
Li et al., "Novel Blood-Compatible Polyurethanes Containing Poly(butadiene) Soft Segments and Phosphatidylcholine Analogues for Biomedical Applications", Chem., Mater., 8, 1441–1450 (1996).
Meijs et al., "Polyurethane Elastomers Containing Novel Macrodiols I. Synthesis and Properties"; Fourth World Biomaterials Congress; April 24–28, 1992; Berlin, Federal Republic of Germany; pp. 473.
Ward et al., "The Effect of Phase Separation and End Group Chemistry on In Vivo Biostability of Polyurethanes", ASAIO (1996), Washington, D.C.
Ward et al., "Thermoplastic Siloxane-Urethane Block Copolymers and Terpolymers for Biochemical Use"; Third World Biomaterials Congress; April 21–25, 1988; Kyoto, Japan; pp. 433.
Yokelson et al., "New Hydrocarbon-based Diols for Polyurethane TABLE 1c-continued Nonpatent Documents Elastomers", Polyurethanes 95: Proceedings of the Polyurethanes 1995 Conference Sponsored by the SPI Polyurethanes Division; September 26–29, 1995; Chicago, Illinois; pp. 100–108.

SUMMARY OF THE INVENTION

The present invention relates to medical devices comprising biomaterials formed from a segmented polymer comprising urethane groups and saturated linear polyethylene units having greater than about 12 carbon atoms (i.e., 12 methylene units) in the chain per polyethylene unit. Both the urethane groups and the saturated linear polyethylene units can provide crystallinity to the polymer. Crystalline segments are desirable because they are generally less susceptible to hydrolysis or oxidation and add strength.

Significantly, the saturated linear polyethylene moieties have no ester, ether, carbonate, amide, or unsaturated groups that may contribute to hydrolytic and/or oxidative instability. They also are relatively long (greater than about 12, preferably at least about 20, and more preferably, at least about 35 carbon atoms in the chain), which can result in fewer urethane groups in the polymer. Because urethane groups can contribute to hydrolytic and/or oxidative instability, the polymers used in the medical devices of the present invention provide a desirable balance between mechanical properties, such as tensile strength and/or modulus of elasticity, and stability. The polymers are also preferably substantially free of ester and ether linkages. They are also preferably substantially free of sulfur- and phosphorus-containing groups.

Preferably, the medical devices of the present invention include, for example, stents, vascular grafts, stent grafts, medical electrical leads, indwelling catheters, balloons, and the like. Preferably, the medical device of the present invention include medical electrical leads (e.g., pacing leads) as the insulation. Thus, the present invention provides a medical electrical lead comprising: an elongated insulation sheath biomaterial formed from a segmented polymer comprising urethane groups and saturated linear polyethylene units having greater than about 12 carbon atoms per unit; an elongated conductor, located within the elongated insulation sheath; an electrode coupled to a distal end of the elongated conductor; and an electrical connector coupled to a proximal end of the elongated conductor.

The present invention also provides a method of using a medical device, particularly a medical electrical lead, comprising the biomaterials described above. The method includes: providing a medical electrical lead comprising an elongated insulation sheath biomaterial formed from a segmented polymer comprising urethane groups and saturated linear polyethylene units having greater than 12 carbon atoms per unit; electrically connecting a first end of the medical electrical lead to implantable medical device; and electrically stimulating or sensing a second end of the lead.

As used herein, "segmented polymer" refers to a polymer having two or more chemically different sections of a polymer backbone that provide separate and distinct properties. These two sections may or may not phase separate. A "crystalline" material is one that has ordered domains (i.e., aligned molecules in a closely packed matrix), as evidenced by Differential Scanning Calorimetry, without a mechanical force being applied. A "noncrystalline" material is one that is amorphous at ambient temperature. A "crystallizing" material is one that forms ordered domains without a mechanical force being applied. A "noncrystallizing" material is one that forms amorphous domains and/or glassy domains in the polymer at ambient temperature.

As used herein, a "biomaterial" may be defined as a material that is substantially insoluble in body fluids and tissues and that is designed and constructed to be placed in or onto the body or to contact fluid or tissue of the body. Ideally, a biomaterial will not induce undesirable reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; can be purified, fabricated and sterilized easily; and will substantially maintain its physical properties and function during the time that it remains implanted in or in contact with the body. An "elastomer" is a polymer that is typically capable of being stretched to approximately twice its original length and retracting to approximately its original length upon release.

As used herein, a "medical device" may be defined as a device that has surfaces that contact blood or other bodily fluids in the course of their operation, which fluids are subsequently used in patients. This can include, for example, extracorporeal devices for use in surgery such as blood oxygenators, blood pumps, blood sensors, tubing used to carry blood and the like which contact blood which is then returned to the patient. This can also include endoprostheses implanted in blood contact in a human or animal body such as vascular grafts, stents, stent grafts, medical electrical leads, indwelling catheters, heart valves, and the like, that are implanted in blood vessels or in the heart. This can also include devices for temporary intravascular use such as catheters, guide wires, balloons, and the like which are placed into the blood vessels or the heart for purposes of monitoring or repair.

DETAILED DESCRIPTION OF THE INVENTION

Figure 1:
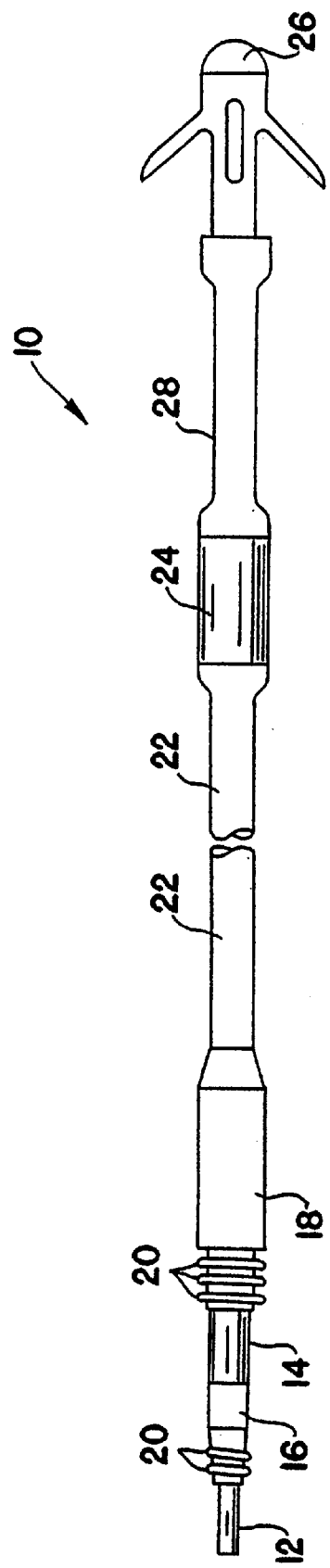
FIG. 1 is a plan view of a medical electrical lead using a segmented polyurethane biomaterial.
Figure 2:
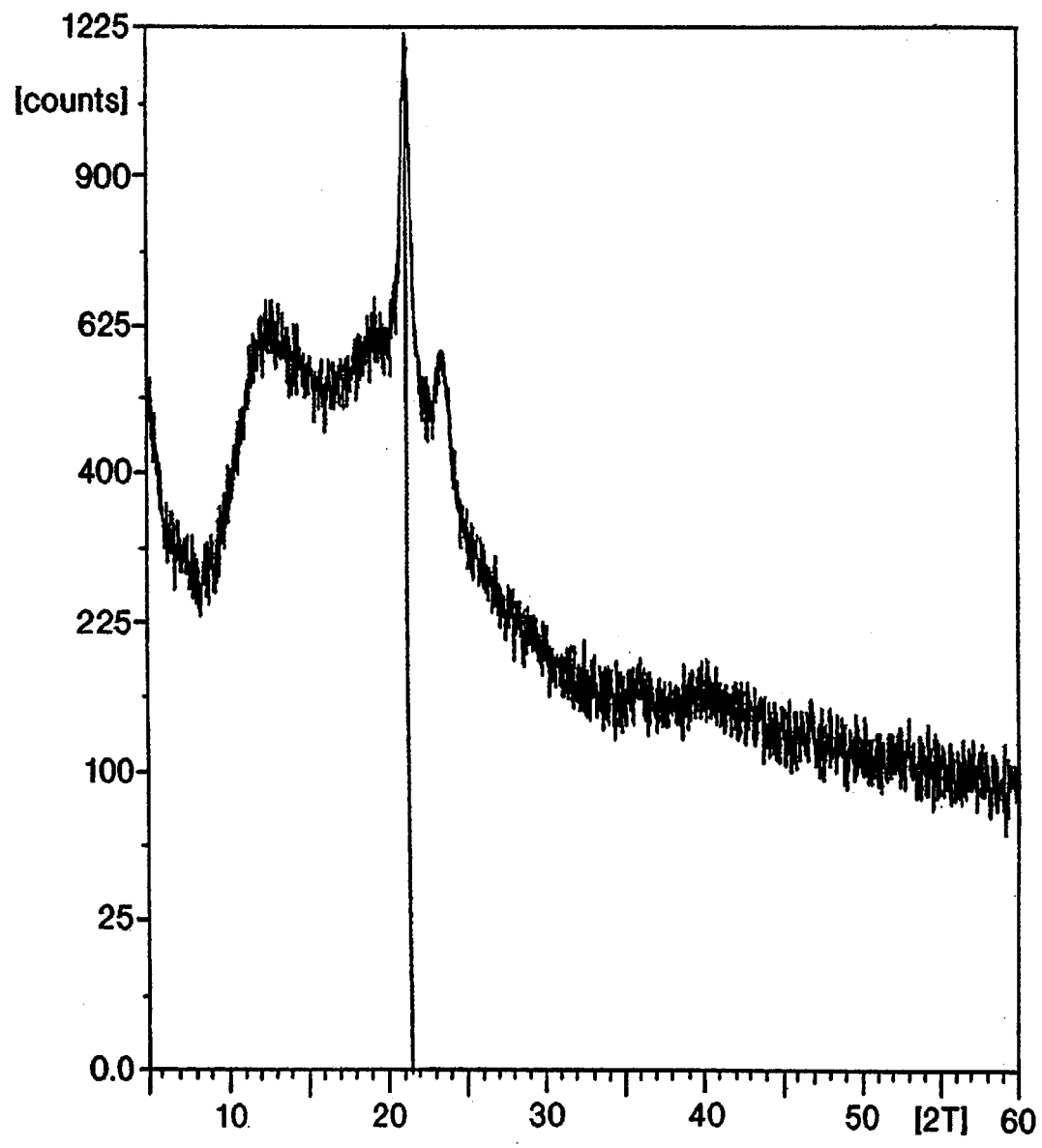
FIG. 2 is an X-ray Diffraction Pattern of a polymer used in the medical decies of the present invention showing crystallinity of both polyurethane and polyethylene character.
Figure 3:
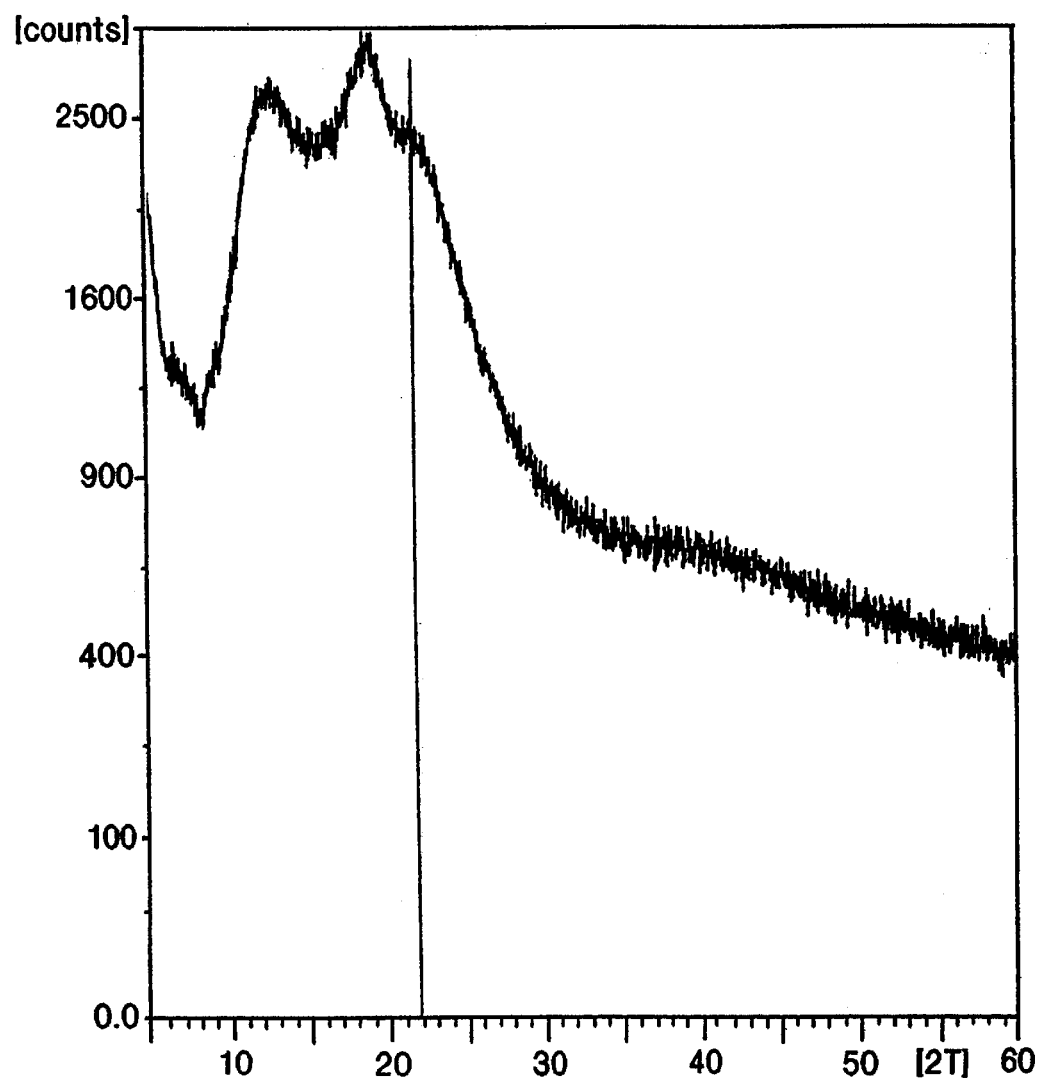
FIG. 3 is an X-ray Diffraction Pattern of another polymer used in the medical devices of the present invention showing crystallinity of both polyurethane and polyethylene character.
Figure 4:
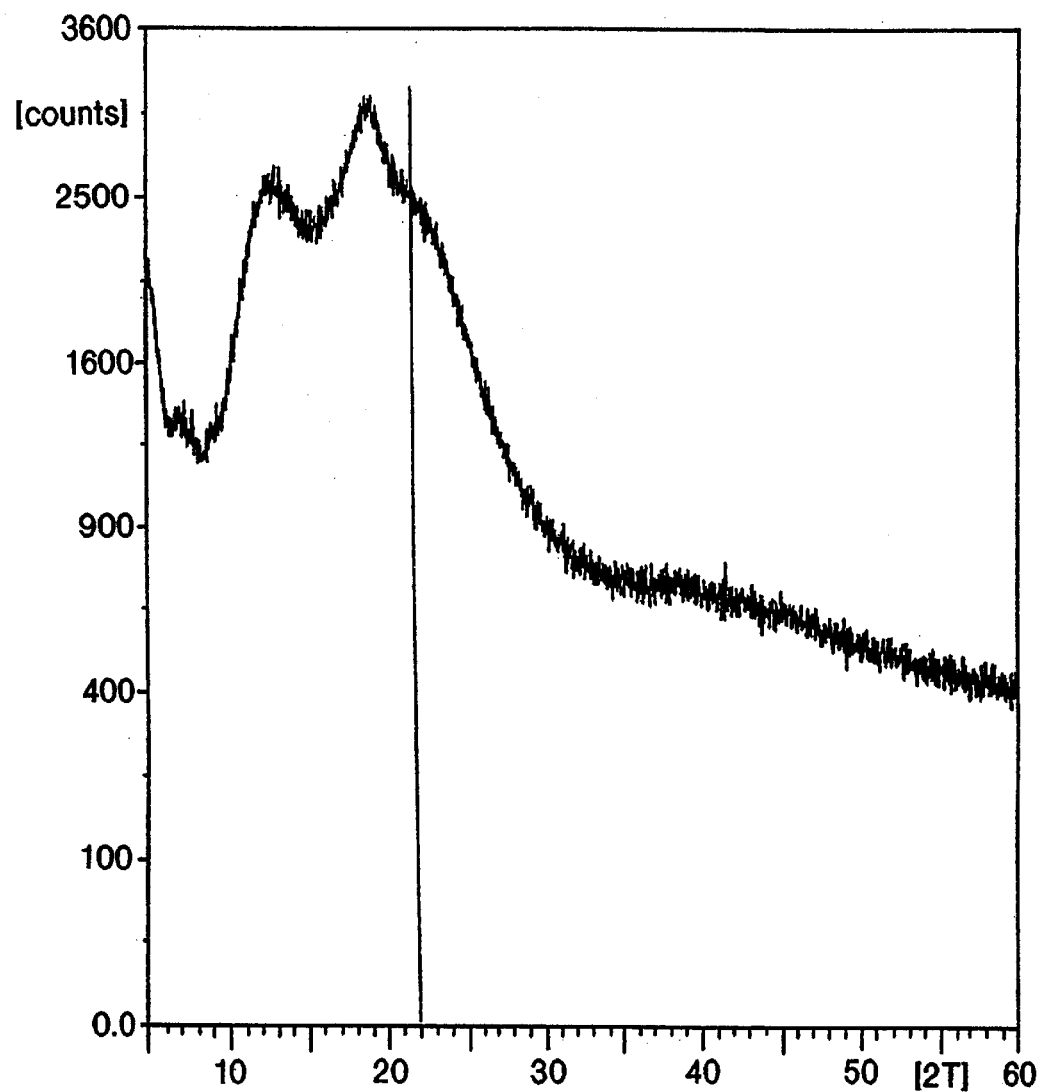
FIG. 4 is a comparative X-ray Diffraction Pattern of a polymer prepared from 1,12-dodecanediol showing crystallinity of only polyurethane character.

The present invention provides medical devices containing segmented polymers that include urethane groups and saturated linear polyethylene units having greater than about 12 carbon atoms (methylene units) in the chain. Preferably, the saturated linear polyethylene units form hard segments (i.e., segments that are substantially crystalline at the temperature of use) that phase separate from soft segments. These segments have crystallinity that is characterized as polyethylene-like, and provide significant advantage to the polymers of the present invention. These polymers can vary from hard and rigid to soft and flexible. Preferably, the polymers are elastomers and include both hard and soft segments.

The saturated linear polyethylene units (i.e., moieties) are derived from linear polyethylene diols, referred to herein as LPE-Diols. They typically impart stronger properties, particularly higher tensile strength and modulus of elasticity, for example, to the polymers of the present invention. Significantly, the polymers of the present invention have an elongation of greater than 50%, and preferably at least about 100%. Saturated linear polyethylene units add improved extensibility when compared to shorter chain linear aliphatic chains, such as 1,12-dodecanediol. Typically, the hard segment in a segmented polyurethane provides strength but without significant extensibility. If the hard segment were to be used by itself, its lack of extensibility would result in a very brittle polymer, one which would not be acceptable for most industrial applications. To overcome this lack of extensibility, a soft segment is included in the polyurethane formulation. Although soft segments do not provide the same degree of strength, they do provide improved extensibility. Such a combination of hard and soft segments provides the balance between strength and flexibility necessary for most applications. Surprisingly, the LPE-Diol formulations, Example No. 22 and Example No. 23, when formulated as hard segments with MDI (no soft segment) show extensibility in excess of 100%. This compares to a 1,12-dodecanediol formulation No. 21, which has an extensibility of 50%. Thus, the use of LPE-Diols adds a level of extensibility to the hard segment which makes the hard segment more acceptable as a useful material even though it contains no soft segment. Although the LPE-Diols are by definition hard segment contributors, they also function in a secondary role as soft segment contributors and can be considered pseudo-soft segments.

The saturated linear polyethylene units also contribute to easier processing of the polymers. Also, polymers can be prepared with saturated linear polyethylene units that have significantly incompatible hard and soft segment domains. This results in phase separation that can occur rather quickly, which contributes to easier processing, reduced surface blocking (e.g., less than about 10 pounds force), and dimensional stability.

Typically, the crystalline melt temperatures of the polymers of the present invention are no greater than about 200° C. The crystalline structure shows both urethane and polyethylene-type crystallinity, as seen in the X-ray diffraction patterns (see, FIGS. 1 and 2 and 3–5 for comparison purposes). In the polymers of the present invention, it is believed that methylene chain lengths of greater than about 12 $CH_2$ units (on average) is sufficiently long to organize as polyethylene crystallites.

Therefore, polyurethane formulations containing such polyethylene units having greater than about 12 carbon atoms in the chain will have some polyethylene character as well as polyurethane character. Thus, the crystallinity of the polymers of the present invention is based in part on the ability of the saturated linear polyethylene moieties to crystallize. This crystallinity is generally independent of the effects that hydrogen bonding has on the crystallization of urethane groups or diisocyanates and on the ultimate crystallinity or crystalline melt of the elastomer.

The polymers are segmented, but they may not necessarily have alternating hard and soft segments that phase separate. That is, the polymers have two or more chemically different sections of their backbones that provide separate and distinct properties but may or may not phase separate. In certain preferred embodiments, however, they do contain both hard and soft segments, wherein the hard segments include saturated linear polyethylene moieties having greater than about 12 carbon atoms (or methylene groups) in the chain. As used herein, a "hard" segment is one that has a relatively higher concentration of crystalline groups (either polyethylene groups or urethane groups) and hence is either crystalline at ambient temperature or amorphous with a glass transition temperature above ambient temperature, and a "soft" segment is one that has a relatively lower concentration of crystalline groups and hence is amorphous with a glass transition temperature below ambient temperature. A crystalline moiety or segment is one that adds considerable strength and higher modulus to the polymer. Similarly, a noncrystalline moiety or segment is one that adds flexibility and lower modulus, but may add strength particularly if it undergoes strain crystallization, for example. The random or alternating soft and hard segments are linked by urethane groups and the polymers may be terminated by hydroxyl, amine, and/or isocyanate groups.

Preferably, both the hard and soft segments are themselves substantially ether- and ester-free. Herein, a substantially ether-free polymer or segment thereof is substantially free of R—O—R linkages (i.e., ether linkages containing an oxygen), and a substantially ester-free polymer or segment thereof is substantially free of R(O)—O—R linkages (i.e., ester linkages containing only oxygen). Furthermore, preferably, both the hard and soft segments are substantially free of sulfur- or phosphorus-containing groups.

A preferred source of saturated linear polyethylene moieties has the following formula:

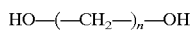

wherein n is greater than about 12 (on average). Preferably, n is at least about 20, and more preferably, at least about 35. Typically, n is no greater than about 1000, preferably no greater than about 140, and more preferably, no greater than about 45. Such diols are typically referred to as linear polyethylene diols or "LPE-Diols" and form the saturated linear polyethylene moieties described above. They are of a generally high molecular weight. Typically, the number average molecular weight is greater than about 200, preferably, greater than about 500, and more preferably, greater than about 1000. The polydispersity (i.e., ratio of number average to weight average molecular weights) is typically within a range of about 1 to about 5, and preferably, about 1 to about 2. Examples include 1,14-tetradecane diol, 1,16-hexadexane diol, 1,20-eicosanediol, hydroxytelechelic polyethylene with an average methylene unit length of 111. The LPE-diols are referred to herein by their molecular weights.

Such LPE-Diols can be synthesized according to the procedures of Fraser et al., *Macromolecules*, 28, 7256–7261 (1995), Hillmyer et al., *Macromolecules*, 25, 872–874 (1993), Hillmyer et al., *Macromolecules*, 28, 8662–8667 (1995), and Hillmyer et al., *Polymer Preprints*, 34, 388–389 (1993). Modified procedures of these syntheses are described herein. Basically, these LPE-diols are synthesized using Ring Opening Methathesis Polymerization (ROMP) or Acylicdiene Methathesis (ADMET) technologies. The ROMP technique uses a ruthenium metal carbene complex that will ring open and polymerize strained cyclic unsaturated olefins such as cyclooctadiene or cyclooctene in the presence of a chain transfer agent such as 1,4-diacetoxy-2-butene to give a diacetoxy protected unsaturated hydroxyl telechelic hydrocarbon. This unsaturated telechelic hydrocarbon is then deprotected and hydrogenated to give the corresponding hydroxytelechelic polyethylene. This diol is essentially difunctional, completely saturated, and linear (nonbranched). The molecular weights of the LPE-diols can be controlled through the ratio of chain transfer agent to cyclic olefin.

Although polyurethane polymers prepared from a wide variety of aliphatic straight chain, branched, and cyclic diols and diisocyanates, as well as aromatic diols and diisocyanates are disclosed in U.S. Pat. No. 4,873,308 (Coury et al.), there is no specific recognition of the advantages of this class of diols. The use of this specific class of LPE-Diols reduces the number of urethane groups within the hard segments, thereby reducing the potential for thermal, oxidative, or hydrolytic instability. The ability to retain strength and modulus properties at a lower urethane level was achieved through the inherent ability of the LPE-Diols to crystallize and form hard segment domains. The incompatibility of these hard segment domains from soft segment domains results in phase separation, which reduces surface blocking and helps promote stabilization of properties such as dimensional stability. Also, a lower number of urethane groups in the hard segments reduces susceptibility of the polymer to hydrolysis and oxidation, particularly during thermal processing.

The use of these LPE-Diols also results in hard segments that are less compatible with the soft segments, and hence, less soluble. This is advantageous because phase separation will occur more quickly. A polyurethane that phase separates and develops crystallinity quickly processes more easily. Furthermore, parts made from polyurethanes of the present invention will block less, need shorter processing times, and require less annealing time.

It should be understood, however, that diols that do not contain saturated linear polyethylene moieties can also be used, as long as the resultant polyurethane includes at least some saturated linear polyethylene moieties having greater than about 12 carbon atoms. Preferably, the polymer includes at least about 1 weight percent saturated linear polyethylene moieties having greater than 12 carbon atoms, based on the total weight of the polymer. More preferably, the polymer includes at least about 30 weight percent saturated linear polyethylene moieties having greater than 12 carbon atoms, based on the total weight of the polymer. Typically, the polymer includes no more than about 99 weight percent saturated linear polyethylene moieties having greater than 12 carbon atoms, based on the total weight of the polymer.

Also, other polyols can be used to form the hard segments (or soft segments), including polyester and polyether polyols, for example, although such polyols are less preferred because they produce less biostable materials. Furthermore, the polyols can be aliphatic (straight, branched, or cyclic aliphatic), aralphatic, and aromatic (including heterocyclic). Examples of suitable materials include 1,10-decane diol, 9-hydroxymethyl octadecanol, cyclohexane-1,4-diol, cyclohexane-1,4-bis(methanol), cyclohexane-1,2-bis(methanol), ethylene glycol, propylene glycol, trimethylene glycol, 1,2-butylene glycol, 1,3-butane diol, 1,4-butane diol, 1,5-pentane diol, 1,2-hexylene glycol, 1,2-cyclohexane diol, 2-butene-1,4-diol, 1,6-hexane diol, 7diol derivative of dimer acid (DIMEROL), and so forth.

Suitable isocyanate-containing compounds for preparation of hard segments (or soft segments) of segmented polyurethanes, are typically aliphatic, cycloaliphatic, araliphatic, aromatic, and heterocyclic polyisocyanates. In addition to the isocyanate groups they can include other functional groups such as biuret, urea, siloxane, etc., that are typically used in biomaterials. Suitable examples of polyisocyanates include 4,4'-methylene bis(phenylisocyanate) (MDI), 4,4'-methylene bis(cyclohexyl isocyanate) (HMDI), paraphenylene diisocyanate, cyclohexane-1,4-diisocyanate, cyclohexane-1,2-diisocyanate, isophorone diisocyanate, hexamethylene-1,6-diisocyanate, tolylene diisocyanates, naphthylene diisocyanates, benzene-1,4-diisocyanate, xylene diisocyanates, diisocyanate derivative of dimer acid (DDI), and so forth.

In the segmented polymers of the invention, the soft segments can be any of those typically used in segmented polyurethanes, such as those disclosed in U.S. Pat. No. 4,873,308 (Coury et al.). The soft segments can include ether groups, ester groups, carbonate groups, branched hydrocarbon groups, silicone groups, and the like. Such groups are noncrystallizing. For example, the soft segments can be based upon noncrystallizing hydrocarbon backbones such as dimer acid derivatives, linked by urethane groups to short and/or medium chain length hydrocarbon moieties. The soft segments can also be derived from siloxane diols such as polydimethyl siloxane diol, polyether diols such as polytetramethylene ether glycols, polyester diols such as polyethylene/polypropylene adipate glycol polyester diol, and polycaprolactone polyester diol, and the like. Siloxane diols are preferred for enhanced stability relative to hydrolysis and oxidatoin. Such diols include methyl, phenyl, propyl, etc. substitution and also include carbonol termination that may include any number of methylene units as desired.

In some embodiments, it is desirable to include short chain hydrocarbon moieties in the relatively soft segment. These short hydrocarbon moieties may be derived from short chain diols, diamines, and/or diisocyanates having chain lengths of 2–6 carbons between the hydroxyl or amine groups. Diols are generally preferred. In some embodiments, inclusion of such short chain hydrocarbon moieties appears to enhance mechanical properties without unduly reducing flexibility. The hydrocarbon moieties in either the hard or soft segments should not be construed to be limited to a particular or single hydrocarbon moiety, but may include one or more different hydrocarbon moieties. In some embodiments, a mix of short and medium chain hydrocarbon moieties is believed desirable.

Preferably, the soft segments of the polymers of the present invention include silicone groups such as those derived from polydimethyl siloxane diols or other siloxane diols. Silicone-containing segments contribute to the stability of the polymer relative to hydrolysis and oxidation. Preferably, the polymer includes at least about 1 weight percent silicone segments, based on the total weight of the polymer. More preferably, the polymer includes at least about 45 weight percent silicone segments, based on the total weight of the polymer. Typically, the polymer includes no more than about 70 weight percent silicone segments, based on the total weight of the polymer. Preferably, the polymer includes no more than about 60 weight percent silicone segments, based on the total weight of the polymer.

The polymers described herein may be isocyanate, hydroxyl, and/or amino terminated depending on the stoichiometric amounts of monomers used. The polymers described herein may be prepared using a one- or a two-stage process either in solution or in bulk, as described in the Examples. In a one-stage process, all the reactants are blended together and allowed to polymerize in a random fashion.

The polymers produced according to the examples outlined below have been found to demonstrate improved stability to oxidation. As a result, they are particularly appropriate for use in implantable devices. They are also believed to be substantially superior to presently available polyurethane formulations.

An example of a medical device for which the polymers are particularly well suited is a medical electrical lead, such as a cardiac pacing lead, a neurostimulation lead, leads employing electrical transducers, etc. Examples of such leads are disclosed, for example, in U.S. Pat. Nos. 5,040,544 (Lessar et al.), 5,375,609 (Molacek et al.), 5,480,421 (Otten), and 5,238,006 (Markowitz). An example of a medical electrical lead is shown in FIG. 1. The pacing lead 10 includes a connector assembly at its proximal end, including a first conductive surface 12, a second conductive surface 14, and two insulative segments 16 and 18. Insulative segments 16 and 18 are each provided with a plurality of sealing rings 20. Extending from the connector assembly is an elongated lead body, including an outer insulative sheath 22, which is formed from the polymers described above. Within insulative sheath 22 is located an elongated conductor (not shown), such as a quadrifilar, multiconductor coil, which is described in U.S. Pat. No. 5,040,544 (Lessar et al.). Two of the conductors within the coil are coupled to conductive surface 12, and the other two are coupled to conductive surface 14. At the distal end of the lead are located a ring electrode 24, coupled to two of the conductors, and a tip electrode 26, coupled to the other two of the four conductors of the quadrifilar coil. Extending between ring electrode 24 and tip electrode 26 is an additional insulative sheath 28. Such medical electrical leads can be implanted into a vein or artery of a mammal and electrically connected to an implantable medical device.

The invention has been described with reference to various specific and preferred embodiments and will be further described by reference to the following detailed examples. It is understood, however, that there are many extensions, variations, and modification on the basic theme of the present invention beyond that shown in the examples and detailed description, which are within the spirit and scope of the present invention.

EXAMPLES

General Synthesis of Hydrocarbon Dialcohols

Undecylenyl acetate was purchased from Bedoukian Research Inc. (Danbury, Conn.). Bis (tricyclohexylphosphine)benzylidine ruthenium (IV) dichloride (Ru catalyst) was purchased from Strem Chemicals Inc. (Newburyport, Mass.). cis-1,4-Diacetoxy-2-butene was purchased from Narchem Corporation (Chicago, Ill.). Cyclooctene was purchased from Fluka Chemical Corporation (Ronkonkoma, N.Y.). Ion-exchange resin, alumina, ALIQUATE 336, and solvents were purchased from Aldrich Chemical Company, Inc. (Milwaukee, Wis.). The ion-exchange resin used was AMBERLITE IRC-718 and was ground in a pebble mill to a fine powder before use. The alumina used was activated, neutral alumina of activity grade Brockmann I. All glassware was flame or oven dried before use.

Synthesis of 1,20-Eicosanediol

Dimerization of Undecylenyl Acetate: A five liter single-neck round bottom flask was outfitted with a magnetic stirbar and placed on a stirplate. A chromatography column with outside diameter about three inches was attached to a vacuum adapter. This adapter was then placed in the neck of the flask. Alumina was added to the column to a depth of seven inches. Undecylenyl acetate, 2000 g, was added to the column and pulled through the alumina by application of water-aspirator vacuum via the vacuum adapter. The column and adapter were then removed and the undecylenyl acetate sparged with nitrogen for ninety minutes. The sparge tube was removed and five grams Ru catalyst were added rapidly. When the addition was complete, a Vigreux column, eighteen inches long, was attached to the flask. A connecting hose adapter (connected to a vacuum pump) was attached to the Vigreux column and vacuum applied. After the initial foaming had subsided, the solution bubbled steadily, and the pressure steadied at about five Torr. The pressure steadily decreased, and was in the neighborhood of one Torr after two hours. After twenty hours, the solution had solidified. A heating mantle was put under the flask and it was heated gently. As the solution liquified, it bubbled, indicating that the catalyst was still active, and that the reaction had not gone to completion. After a further 24 hours, the solution was a viscous liquid. It was still bubbling, and the pressure was 80 mT. After the reaction had run a total of about 52 hours, the heating mantle was turned off and the reaction was left under passive vacuum for 48 hours. Then six liters of hexanes were added to the reaction, and the solid product dissolved by gentle heating. The bulk of the catalyst was removed by passing through the chromatography column again, this time containing about seven inches neutral alumina and seven inches ion-exchange resin.

Deprotection of Dimer Product (10-eicosene-1,20-diol): The hexanes solution was placed in a twelve liter round bottom flask outfitted with a magnetic stirbar. The hexanes were removed by distillation, and one kilogram sodium hydroxide dissolved in one liter deionized water was added. Forty grams ALIQUAT 336 (tricaprylyl methyl ammonium chloride) was added and a condenser attached to the flask. The reaction mixture was heated with stirring to gentle reflux. After 24 hours, the heating was stopped. The hot solution was poured into a stainless steel container of approximately five gallons capacity. The product crystallized on cooling. The crude product was vacuum filtered from the caustic solution using a Buchner funnel, and then washed with deionized water. The crude product was dissolved in methanol and filtered, and then recrystallized twice from methanol.

Hydrogenation of 10-eicosene-1,20-diol: Two hundred fifty grams of the 10-eicosene-1,20-diol were placed in a twelve liter flask outfitted with a heating mantle, mechanical stirrer, condenser, and nitrogen inlet. Three liters of xylenes were added. Two equivalents each tributylamine and toluenesulfonhydrazide were added. Stirring and nitrogen flow were initiated and the solution slowly heated until the reaction was at reflux. The reaction was refluxed overnight, and then cooled to room temperature. The product, 1,20-eicosanediol, precipitated from solution and was filtered, washing with methanol. The crude product was recrystallized once from methanol, yielding white crystals with a melting point of about 101° C. The product was 99% pure by gas chromatography. IR(KBr): 3419, 3357, 2919, 2848, 1469, 1355, 1321, 1124, 1055, 1034, 999, 969, 722, 610, 502 cm$^{-1}$; $^1$H NMR(300 MHz, toluene-d$_8$, elevated temperature): * 3.3 (t, 4H), 1.3 (bd, 36H), 0.5 (m, 2H).

Synthesis of Higher Molecular Weight Hydrocarbon Dialcohols

Synthesis of hydrocarbon dialcohols: Cyclooctene and cis-1,4-diacetoxy-2-butene (chain transfer agent, CTA) were purified by passage through neutral alumina before use as described above. These materials are added according to the molecular weight desired, but because the catalyst tended to become inactive before the reaction was complete, an excess of about 50% of the CTA was used. A three fitter three neck flask was outfitted with magnetic stirrer, dual adapter with nitrogen sparge and thermometer, and connection to bubbler. To this flask was added the cyclooctene and cis-1,4-diacetoxy-2-butene. This mixture was sparged with nitrogen for 30 minutes. Then 2.25 grams Ru catalyst was added. The sparging was continued for ten minutes and then the sparge tube pulled above the liquid surface and the nitrogen flow rate slowed to about one bubble per second through the bubbler.

The reaction continued over the course of eighteen hours and the reaction mixture became dark brown and viscous. At this point the bulk of the catalyst residue was removed from the reaction mixture by diluting it with three volumes of hexanes and passing it through a chromatography column containing about six inches of neutral alumina and six inches of ion-exchange resin. The solvent and unreacted cyclooctene were removed by rotary evaporation, and unreacted CTA removed by use of a wiped-film still.

Deprotection of Product: Deprotection is done by treating the product with 50% aqueous NaOH and ALIQUAT 336 as described above, yielding hydroxytelechelic polyoctenamer.

Hydrogenation: The hydroxytelechelic polyoctenamer was hydrogenated in a high pressure reactor using 5% palladium on calcium carbonate as catalyst. The catalyst was removed from the resulting hydroxytelechelic polyethylene by hot pressure filtration. The polymer was then ground and extracted with methanol. Alternatively, the hydroxytelechelic polyoctenamer can be hydrogenated using toluenesulfonhydrazide, as described above. IR(KBr): 3340, 2920, 2851, 1464, 1373, 1252, 1121, 1057, 999, 969, 729, 530 cm$^-$; $^1$H NMR (300 MHz, toluene-d$_8$, elevated temperature): * 3.3 (t, 4H), 1.3 (bd), 0.5 (m, 2H).

Examples 1–6

The following examples compare the properties of polyurethane elastomers based on a hard segment comprising MDI and a 1520 MW LPE Diol (Linear Polyethylene Diol) with various soft segments based on PDMS (Silicone), polyether, and polyester based macrodiols.

Example No. 1

One step solution polymerization of LPE-1520 Diol/MDI hard segment (42%) and PDMS Diol soft segment (58%).

Experimental Equipment: Dry box, 1 liter three neck round bottom flask fitted with stirrer, thermometer, nitrogen inlet/outlet and heating mantle. Polymerization was run in a vented hood. Precipitation of the polymer out of solution was done in a waring blender. Dying of the precipitated polymer was done in a vacuum oven.

Materials: Hard segment, LPE-1520 Diol (linear polyethylene diol 1520 grams per mole molecular weight); MDI (4,4'-methylene bis(phenyliisocyanate)), Dow Chemical Co. (Midland, Mich.); soft segment, PDMS diol (polydimethyl siloxane diol), TEGOMER H-Si 2111 Goldschmidt Co. (Hopewell, Va.); catalyst T-9 (stannous octoate), Air Products, Inc. (Allentown, Pa.); anhydrous DMAC (dimethylacidamide), toluene, methanol, all from Aldrich Chemical Co. Inc. (Milwaukee, Wis.).

Mixing Procedure: In a dry box, 13.52 grams of LPE-1520 hard segment diol, 34.78 grams of PDMS soft segment diol, 40 grams of DMAC, and 160 grams of distilled toluene were added to a flame dried 1 liter three neck round bottom flask. The flask was fitted with a stirrer, thermometer, and nitrogen inlet/outlet and transferred from the dry box to a vented hood. The flask was fitted with a heating mantle and heating was initiated with constant stirring. A nitrogen purge was started and continued for 3 to 5 minutes after which it was stopped and the outlet was stoppered, thereby creating a closed system. As the contents of the flask were heated to approximately 85° C. to 95° C., the LPE melted and dissolved producing a clear solution. To this solution were added 100 ml of distilled toluene and 12.55 grams of flaked MDI. The temperature in the flask dropped initially but it eventually returned to its set point of about 90° C. At this point, the mixing was complete and the polymerization started. Mixing time was approximately 24 minutes.

Polymerization Procedure: After the contents of the flask returned to about 90° C., two drops of the polymerization catalyst T-9 was added to the flask. This accelerated the reaction resulting in an exotherm to about 93° C. After about 16 minutes, the reaction was monitored using FTIR to look for a residual NCO. (Note, if there was no NCO peak and the viscosity of the solution indicated a low molecular weight polymer, then additional MDI was added, if there was too great an NCO peak then additional diols, both hard and soft segment, were added.) In this instance, the FTIR scan showed no NCO peak so an additional 0.13 gram of MDI was added to the flask. After 20 minutes, another FTIR scan showed no NCO peak. At this point the reaction was terminated by quenching it in methanol and precipitating the polymer out of solution. Total reaction time was 36 minutes.

Precipitation Procedure: The polymer was precipitated by pouring it into a mixture of methanol and water (4/1 ratio). A waring blender was filled half way with pure methanol. The blender was started and the solution from the reaction flask was slowly poured into the methanol after which water was added to insure a more complete precipitation. The solids were filtered and then added to a blender half filled with pure methanol to wash out any retained solvents. This washing procedure was done two times after which the solids were dried in a vacuum oven at 50° C. for approximately 7 hours.

Testing of Polymer: The dried polymer powder was compression molded into films at approximately 180° C. and annealed for 7 hours at 70° C. following the process described below. Dog Bones were cut from 25 mil (0.064 cm) sheets using an ASTM D412 die or an ASTM D1708 die, and tested for physical properties using a SYNTECH 1D machine according to ASTM D412 at 10 inches (25.4 cm) per minute crosshead speed, or ASTM D-1708 at 5 inches (12.7 cm) per minute crosshead speed, for stress-strain properties and ASTM D624 Die B, 20 inches (50.8 cm) per minute crosshead speed, for tear strength. Results of the physical testing are presented below in Table 3.

Compression Molding Process: The compression molding process was preheated to the desired temperature. Typically, to produce a 6 inch by 6 inch (15 cm×15 cm) sheet of standard thickness 25 mils (0.064 cm), about 20 grams of polymer granules were used. This amount may be adjusted for other film thickness. The granules were molded between ferrotype photographic plates lined with ARMALON TEFLON coated fiberglass cloth. The assembled molding plates and polymer were placed between the platens of the press, and pressed under 20,000 pounds ram force, without preheating the polymer. Pressure was maintained until the pressure drops between the plates ceased, indicating no further flow of the polymer (typically 30–60 seconds). The pressure was then released and the polymer was immediately quenched to room temperature between 1 inch (2.5 cm) thick aluminum plates. The molded polymer was allowed to sit at ambient conditions for at least 24 hours prior to any testing. If desired, the polymer can be annealed after molding by placing it into a forced air oven at 70° C. for up to 24 hours.

Example No. 2

One step solution polymerization of LPE-1520 Diol/MDI hard segment (42%) and PTMEG 1000 diol soft segment (58%).

Experimental Equipment: The same as for Example No. 1.

Materials: The same as for Example No. 1 except the soft segment diol was PTMEG 1000 polytetramethylene ether glycol of MW 1000, Quaker Oats (West Lafayette, Ind.).

Mixing Procedure: The mixing procedure was the same as in Example No. 1. The reactants were as follows: 14.1 grams of hard segment diol LPE-1520, 34.92 grams of soft segment diol PTMEG, 63 grams of anhydrous DMAC, 200 grams of distilled toluene, 10.00 grams of flaked MDI, 50 ml of distilled toluene. Total mixing time was 46 minutes.

Polymerization Procedure: The polymerization procedure was the same as in Example No. 1. After 26 minutes, the reaction was monitored for NCO by FTIR. The FTIR scan showed a small NCO peak. At this point the reaction was terminated. Total reaction time was 26 minutes.

Precipitation Procedure: The precipitation procedure was the same as described in Example No. 1. The polymer solids were dried in a vacuum oven at 60° C. for 4 hours.

Testing of Polymer: The dried polymer was compression molded into film at approximately 180° C. and annealed overnight at 70° C. following the process described in Example No. 1. All physical property testing was done according to the procedures described in Example No. 1. The results of that testing are presented in Table 3.

Example No. 3

One step solution polymerization of LPE-1520 Diol/MDI hard segment (42%), and FORMREZ A23, a polyethylene/polyproylene adipate glycol polyester diol soft segment of MW 1820 (58%), from Witco Chemical Co. (Greenwich, Conn.).

Experimental Equipment: The same as for Example No. 1.

Materials: The same as for Example No. 1 except the soft segment diol was FORMREZ A23 (adipate polyester diol).

Mixing Procedure: The mixing procedure was the same as in Example No. 1. The reactants were as follows: 17.5 grams of hard segment diol LPE-1520, 34.82 grams of soft segment diol FORMEZ A23, 40 grams of anhydrous DMAC, 326 grams of distilled toluene, 7.85 grams flaked MDI, 40 grams of distilled is toluene. Total mixing time was 50 minutes.

Polymerization Procedure: The polymerization procedure was the same as in Example No. 1. After 49 minutes, an FTIR scan showed a large NCO peak. Additional diols were added to the reaction, 1.01 grams of LPE, and 0.95 gram of FORMEZ A23. After 50 minutes, an FTIR scan showed a smaller but still too large NCO peak. Additional LPE diol, 0.95 gram, was added to reaction. After 20 minutes an FTIR scan showed no significant change in NCO peak. Additional FORMEZ A23, 1.25 grams, was added to the reaction. After 40 minutes an FTIR scan showed a small NCO peak. At this point the reaction was terminated. Total reaction time was 159 minutes.

Precipitation Procedure: The precipitation procedure was the same as described in Example No. 1.

Testing of Polymer: The dried polymer was compression molded into films following the process described in Example No. 1. All physical property testing were done according to the procedures described in Example No. 1. The results of that testing are presented in Table 3.

Example No. 4

One step solution polymerization of LPE-1520 Diol/MDI hard segment (42%) and TONE 2221 polycaprolactone polyester diol of MW 1000, Union Carbide (58%).

Experimental Equipment. The same as for Example No. 1.

Materials: The same as in Example No. 1 except the soft segment diol was TONE 2221 polycaprolactone polyester diol soft segment.

Mixing Procedure: The mixing procedure was the same as in Example No. 1. The reactants were as follows: 14.00 grams of hard segment diol LPE-1520, 34.83 grams of soft segment diol TONE 2221, 40 grams of anhydrous DMAC, 200 grams of distilled toluene, 11.40 grams flaked MDI, 40 grams of distilled toluene. Total mixing time was 30 minutes.

Polymerization Procedure: The polymerization procedure was the same as in Example No. 1. After 40 minutes, an FTIR scan showed no NCO peak. LPE diol, 1.38 grams, and TONE 2221 diol, 0.90 gram, were added to the reaction. After 13 minutes an FTIR scan showed an NCO peak slightly larger than desired. LPE diol, 1.38 grams, was added to the reaction. After 42 minutes an FTIR scan showed a very small NCO peak. The reaction was terminated. Total reaction time was 95 minutes.

Precipitation Procedure: The same as described in Example No. 1. The polymer solids were dried in a vacuum oven at 50° C. overnight.

Testing of Polymer: The dried polymer was compression molded into films at approximately 190° C. and annealed overnight at 70° C. following the process described in Example No. 1. All physical property testing were done according to the procedures described in Example No. 1. The results of that testing are presented in Table 3.

Example No. 5

One step solution polymerization of LPE-1520 Diol/MDI hard segment (42%) and TONE 2241 polycaprolactone polyester diol of MW 2000, Union Carbide (58%).

Experimental Equipment: The same as for Example No. 1.

Materials: Hard segment diol, diisocyanate, polymerization catalyst, and solvents were the same as in Example No. 1. The soft segment diol was TONE 2241 polycaprolactone polyester diol.

Mixing Procedure: The mixing procedure was the same as in Example No. 1. The reactants were as follows: 17.84 grams of hard segment diol LPE, 34.82 grams of soft segment diol TONE 2241, 40 grams of anhydrous DMAC, 200 grams of distilled toluene, 7.5 grams of flaked MDI, and 40 grams of distilled toluene.

Polymerization Procedure: The polymerization procedure was the same as in Example No. 1. The exothermic temperature rose from 91° C. to 94° C. After 27 minutes, an FTIR scan showed a small to medium sized NCO peak. LPE diol, 1.82 grams, and TONE 2241 diol, 1.17 grams, were added to the reaction. After 40 minutes, an FTIR scan showed a small NCO peak. The reaction was terminated. Total reaction time was 67 minutes.

Precipitation Procedure: The same as described in Example No. 1. The polymer solids were dried in a vacuum oven at 60° C. for 3 hours.

Testing of Polymer: The dried polymer was compression molded into films and annealed for 18 hours at 70° C. following the process as described in Example No. 1. An FTIR scan on a 3 mil (0.008 cm) film showed no residual NCO peak. All physical property testing were done according to the procedures described in Example No. 1. The results of that testing are presented in Table 3.

Example No. 6

One step solution polymerization of LPE-1520 Diol /MDI hard segment (42%) and PTMEG 650 diol soft segment (58%).

Experimental Equipment: The same as for Example No. 1.

Materials: The hard segment diol, diisocyanate, polymerization catalyst, and solvents were the same as in Example No. 1. The soft segment diol was PTMEG 650 polytetramethylene ether glycol soft segment of MW 650, Quaker Oats.

Mixing Procedure: The mixing procedure was the same as in Example No. 1. The reactants were as follows: 10.39 grams, of hard segment diol LPE, 34.85 grams of soft segment diol PTMEG 650, 40 grams of anhydrous DMAC, 200 grams of distilled toluene, 15.67 grams of flaked MDI, and 40 grams of distilled toluene. Total mixing time was 28 minutes.

Polymerization Procedure: The polymerization procedure was the same as in Example No. 1. The exothermic temperature was not recorded. After 37 minutes, an FTIR scan showed a very small NCO peak. The reaction was terminated. Total reaction time was 37 minutes.

Precipitation Procedure: Same as described in Example No. 1 except hexanes, methanol, and wet acetone were used as the precipitation solvents. The polymer solids were dried in a vacuum oven at 50° C. overnight.

Testing of Polymer: The dried polymer was compression molded into films at approximately 150° C. and annealed at 70° C. for 24 hours following the process described in Example No. 1. An FTIR scan on a 3 mil (0.008 cm) film showed no residual NCO peak. All physical property testing was done according to the procedures detailed in Example No. 1. The results of that testing are presented in Table 3.

Examples 7–11

The following examples compare the properties of polyurethane elastomers based on a soft segment comprising PDMS, polydimethyl siloxane diol (MW 920), and a hard segment based on MDI as the isocyanate and a LPE hard segment diol in which the carbon chain length varied.

Example No. 7

One step solution polymerization of LPE-860 Diol /MDI hard segment (42%) and PDMS Diol soft segment (58%).

Experimental Equipment: The same as for Example No. 1.

Materials: The same as for Example No. 1 except the hard segment diol was LPE-860 Diol, MW 860. In addition to polymerization catalyst T-9, T-12 (dibutytin dilaurate) from Aldrich Chemical Co. was used as a co-catalyst.

Mixing Procedure: The mixing procedure was the same as for Example No. 1. The reactants were as follows: 12.05 grams of hard segment LPE-860 diol, 34.89 grams of PDMS soft segment diol, 40 grams of anhydrous DMAC, 160 grams of distilled toluene, 13.32 grams of flaked MDI, and 100 ml of distilled toluene. Total mixing time was 40 minutes.

Polymerization Procedure: The polymerization procedure was the same as in Example No. 1. After 1 hour and 45 minutes, an FTIR scan showed no significant change in NCO from the previous FTIR scan, so two drops of catalyst T-12 were added to the reaction. After 52 minutes, an FTIR scan showed no NCO peak. The reaction was terminated. Total reaction time was 157 minutes.

Precipitation Procedure: Same as described in Example No. 1. The polymer solids were dried in a vacuum oven at 50° C. for two hours.

Testing of Polymer: The dried polymer was compression molded into films at approximately 150° C. and annealed for 24 hours at 70° C. following the process described in Example No. 1. All physical property testing was done according to the procedures described in Example No. 1. The results of that testing are presented in Table 3.

Example No. 8 (Comparative)

One step solution polymerization of Butanediol/MDI hard segment (42%) and PDMS diol soft segment (58%).

Experimental Equipment: The same as in Experiment No. 1.

Materials: The same as in Example No. 1 except the hard segment diol was butanediol from Aldrich Chemical Co., MW 90.

Mixing Procedure: The mixing procedure was the same as in Example No. 1. The reactants were as follows: 4.25 grams of hard segment butanediol, 35.50 grams of soft segment PDMS diol, 40 grams of anhydrous DMAC, 160 grams of distilled toluene, 21.51 grams of MDI, and 10 ml of distilled toluene.

Polymerization Procedure: The polymerization procedure was the same as in Example No. 1, except that the reaction temperature was kept generally less than 80° C. The exothermic temperature rose from 61° C. to 67° C. after which the solution gelled. Distilled toluene, 125 ml, and anhydrous DMAC, 20 ml, were added to the reaction to dissolve the gel. After 47 minutes, an FTIR scan showed no residual NCO peak. MDI, 0.44 gram, was added to the reaction. After 20 minutes an FTIR scan showed a very small NCO peak. The reaction was terminated. Total reaction time was 67 minutes.

Precipitation Procedure: The same as described in Example No. 1.

Testing of Polymer: The dried polymer was compression molded into films at approximately 150° C. and annealed at 70° C. overnight following the process described in Example No. 1. All physical property testing were done according to the procedures described in Example No. 1. The results of that testing are presented in Table 3.

Example No. 9

One step solution polymerization of LPE-1596 Diol/MDI hard segment (42%) and PDMS Diol soft segment (58%).

Experimental Equipment: The same as in Example No. 1 except a three liter round bottom flask was used.

Materials: The same as in Example No. 1 except the hard segment diol was LPE-1596 diol, MW 1596.

Mixing Procedure: The mixing procedure was the same as in Example No. 1. The reactants were as follows: 54.17 grams of hard segment diol LPE-1596, 139.28 grams of soft segment diol PDMS, 166 grams of anhydrous DMAC, 960 grams of distilled toluene, 51.21 grams of flaked MDI, and 140 ml of distilled toluene. Total mixing time was 58 minutes.

Polymerization Procedure: The polymerization procedure was the same as in Example No. 1, except three drops of catalyst T-9 were used instead of two drops. After 15 minutes, an FTIR scan showed no residual NCO peak. The reaction was terminated. Total reaction time was 15 minutes.

Precipitation Procedure: The same as described in Example No. 1. The polymer solids were dried in a vacuum oven at 50° C. overnight.

Testing of Polymer: The dried polymer was compression molded into films at approximately 165° C. and annealed at 70° C. for 24 hours following the process described in Example No. 1. Immediately after compression molding, it was noticed that the films did not block to each other. All physical property testing were done according to the procedures described in Example No. 1. The results of that testing are presented in Tables 2 and 3.

Example No. 10 (Comparative)

One step solution polymerization of 1,12-Dodecanediol/ MDI hard segment (42%) and PDMS diol soft segment (58%).

Experimental Equipment: The same as in Example No. 1, except a three liter round bottom flask was using instead of a one liter.

Materials: The same as in Example No. 1 except the hard segment diol was 1,12-dodecanediol obtained from Aldrich Chemical Co.

Mixing Procedure: The mixing procedure was the same as in Example No. 1. The reactants were as follows: 27.98 grams of hard segment diol, 139.30 grams of PDMS soft segment diol, 166 grams of anhydrous DMAC, 960 grams of distilled toluene, 75.66 grams of flaked MDI, and 100 ml of distilled toluene. Total mixing time was 35 minutes.

Polymerization Procedure: The polymerization procedure was the same as in Example No. 1, except four drops of catalyst T-9 were used instead of two drops. After 15 minutes, an FTIR scan showed no NCO peak. Additional MDI, 1.89 grams, was added to the reaction. After 37 minutes an FTIR scan showed a very small NCO peak. The reaction was terminated. Total reaction time was 52 minutes.

Precipitation Procedure: The same as in Example No.1. The polymer solids were dried in a vacuum oven at 50° C. overnight.

Testing of Polymer: The dried polymer was compression molded into films at approximately 180° C. and annealed overnight at 70° C. following the process described in Example No. 1. All physical property testing were done according to the procedures described in Example No.1. The results of that testing are presented in Table 3.

Example No. 11

One step solution polymerization of LPE-314 Diol /MDI hard segment (42%) and PDMS diol soft segment (58%).

Experimental Procedure: The same as in Example No. 1.

Materials: The same as in Example No. 1 except the hard segment diol was LPE-314 diol, MW 314.

Mixing Procedure: The mixing procedure was the same as in Example No. 1. The reactants were as follows: 8.71 grams of hard segment diol LPE-314, 34.81 grams of soft segment diol PDMS, 46 grams of anhydrous DMAC, 240 grams of distilled toluene, 16.81 grams of flaked MDI, and 50 ml of distilled toluene. Total mixing time was 35 minutes.

Polymerization Procedure: The polymerization procedure was the same as in Example No. 1. After 15 minutes, an FTIR scan showed no detectable NCO. Additional MDI, 0.68 gram, was added to the reaction. After 27 minutes, an FTIR scan showed a small NCO peak. The reaction was terminated. Total reaction time was 42 minutes.

Precipitation Procedure: The same as described in Example No. 1. The polymer solids were dried in a vacuum oven at 60° C. overnight.

Testing of Polymer: The dried polymer was compression molded into films and annealed at 70° C. for 24 hours following the process described in Example No. 1. All physical property testing were done according to the procedures described in Example No. 1. The results of that testing are presented in Table 3.

Example 12

The following example showed the affect that increasing the soft segment (PDMS diol) has on the properties of the elastomer. Example No. 11 was at 58% soft segment while Example No. 12 was at 62% soft segment. Both examples used PDMS Diol, MW 960 as the soft segment, LPE diol MW 314, and MDI as the hard segments.

Example No. 12

One step solution polymerization LPE-314 Diol/MDI hard segment (38%) and PDMS diol MW 960, soft segment (62%).

Experimental Equipment: The same as in Example No. 1, except a 3 liter round bottom flask was used instead of a 1 liter.

Materials: The same as for Example No. 11.

Mixing Procedure: The mixing procedure was the same as for Example No. 1. The reactants were as follows: 28.49 grams of hard segment diol LPE-314, 148.24 grams of soft segment diol PDMS, 120 grams anhydrous DMAC, 900 grams of distilled toluene, 66.43 grams of flaked MDI, and 60 grams of distilled toluene. Total mixing time was 51 minutes.

Polymerization Procedure: The polymerization procedure was the same as in Example No. 1. After 14 minutes, an FTIR scan showed no residual NCO peak and no thread development when a sample was pulled from solution, which indicated low molecular weight. Additional MDI, 0.66 gram, was added to the reaction. After 38 minutes, an FTIR scan showed a small NCO peak and the solution showed an ability to make threads. The reaction was terminated. Total reaction time was 52 minutes.

Precipitation Procedure: The same as described in Example No. 1 except acetone was used in addition to methanol and water. The polymer solids were dried in a vacuum oven at 60° C. for 4 hours.

Testing of Polymer: The dried polymer was compression molded into films at approximately 180° C. and annealed at 80° C. for 24 hours. All physical property testing were done according to the procedure described in Example No. 1, except test specimens were run based on dog-bones cut with an ASTM D-637980 8 die and run at 5 inches (12.7 cm) per minute crosshead speed. The results of that testing are presented in Tables 2 and 3.

Example 13

The following example describes a two step solution polymerization procedure for formulating a polyurethane elastomer based on a PDMS Diol as the soft segment (60%), and a 620 MW LPE diol with MDI as hard segments (40%).

Example No. 13

Two step polymerization of LPE-610 Diol/MDI hard segment (40%) PDMS diol soft segment (60%).

Experimental Equipment: The same as for Example No. 1.

Materials: Hard segment diol, LPE-610 Diol of MW 610; MDI from Dow Chemical Co., PDMS soft segment diol of MW 810, TEGOMER H-Si 2111, from Goldschmidt Co., catalyst T-9 (stannous octoate) from Air Products, anhydrous toluene from Aldrich, DMAC from Mallinkrodt, cyclohexane from Mallinkrodt, and acetone/IPA from Aldrich.

Mixing/Polymerization Procedure Step 1: In a one litter flask 90 ml of toluene, 10 ml of DMAC, and 20 ml of cyclohexane were added and heated with stirring to 105° C. so that 11 ml of solvent were distilled off. The flask was transferred to dry box and 31.00 grams of PDMS diol and 12.57 grams of MDI were added. The flask was moved back to the hood and heated with stirring. Temperature set point was 50° C., exothermic temperature was measured at 90° C., and after 5 minutes the temperature dropped to 75° C. Step 2: 6.69 grams of LPE diol plus 100 ml toluene were added to the flask. The contents of flask were heated to 100° C. until LPE diol dissolved and allowed to cool to 80° C. Then two drops of catalyst T-9 were added. After 40 minutes, an FTIR scan showed a large NCO peak. PDMS diol, 0.47 gram, were added to the flask. After two minutes, the polymer solution gelled.

Precipitation Procedure: The gelled polymer solution was added to acetone/IPA to precipitate and then the polymer was dried at 70° in vacuum oven.

Testing of Polymer: The dried polymer was compression molded into films at approximately 210° C. and annealed at 70° C. for 24 hours. All physical property testing was done according to the procedures described in Example No. 1. The results of that testing are presented in Table 3.

Example 14

The following example used a branched cyclic hydrocarbon diisocyanate (Dimer Diisocyanate) available from Henkel Corp. in combination with butanediol as the soft segment components. In this example the LPE diol was the only hard segment contributor.

Example No. 14

One step solution polymerization of LPE-2026 diol hard segment (55%) and DDI 1410 butanediol soft segment (45%).

Experimental Equipment: The same as in Example No. 1.

Materials: Hard segment LPE-2026 diol, MW 2026, soft segment diisocyanate, DDI 1410, MW 592, from Henkel Corp. (Ambler, Pa.), soft segment from butanediol, DMAC, xylene, and acetone, all from Aldrich, cyclohexane from Mallinkrodt. The polymerization catalyst was T-9 (stannous octoate) from Air Products.

Mixing/Polymerization Procedure: Into a 500 ml 3 neck flask were added 50 grams of DMAC, 50 grams of xylene, and 20 ml of cyclohexane. These were heated to 120° C. with stirring and 10 ml of solvent was stripped off in 40 minutes. After distillation, the flask was transferred to the dry box and 28.86 grams of LPE-2026, 2.49 grams of butanediol, and 20.97 grams of DDI-1410 were added to the flask. The flask was transferred to the hood and heated to 100° C. after which two drops of catalyst T-9 were added to the flask. At 102° C. the solution became clear and exothermed to 128° C. The heating mantle was lowered and the solution cooled to the set point, 110° C. After 40 minutes, a second exothermic rise in temperature occurred to 115° C. An FTIR scan showed no NCO peak, so 5.68 grams of DDI-1410 were added to the flask. An FTIR scan showed an NCO peak. Butanediol was then added dropwise (0.24 gram total) until the NCO was reduced to a very small peak and the viscosity of the solution was high.

Precipitation Procedure: The precipitation was in acetone and the procedure was the same as described in Example No. 1. The polymer solids were dried in a vacuum oven at 70° C. for 4 hours.

Testing of Polymer: The dried polymer was compression molded into films at approximately 165C and annealed at 70° C. for 48 hours. All physical property testing was done according to the procedures described in Example No. 1. All thermal property testing was done according to ASTM D-3418 for Tg and Tm, and ASTM D-3417 for enthalpy. The results of that testing are presented in Table 3. Tg −7° C. Tm 120° C.

Examples 15–16

Example 15 describes a process for formulating a polyurethane elastomer containing an LPE diol hard segment component neat (no solvent). The example also contains a branched C36 hydrocarbon diol as a soft segment. Example 16 describes a process for the preparation of an additive-free polyurethane polymer similar to PELLETHANE.

Example No. 15

Neat polymerization of LPE-314 Diol/MDI, hard segment (42%) and C36 branched hydrocarbon diol (PRIPOL 2033) soft segment (58%).

Experimental Equipment: Teflon beaker and a polypropylene stir stick.

Materials: Hard segment diol LPE-314, MW 314, MDI from Dow Chemical, soft segment diol PRIPOL 2033, MW 556, from Unichema (Chicago, Ill.).

Mixing/Polymerization Procedure: In a dry box, LPE-314 diol and PRIPOL 2033 diol were added into a Teflon beaker and transferred to a 100° C. oven in the dry box. After the diols melted, the mixture was stirred to ensure uniformity. The beaker was removed from the oven and flaked MDI was added and then stirred rapidly until the MDI dissolved and the mixture was uniform. The mixture was continuously stirred and the sides of the beaker were wiped with the stir stick. After 3 minutes the mixture was too thick to stir. The stir stick was removed and the beaker placed into a 100° C. oven and allowed to react overnight.

Testing of Polymer: The polymer was compression molded at 190° C. into films and annealed at 80° C. for 24 hours. All physical property testing was done according to the procedures described in Example No. 1. The results of that testing are presented in Tables 2 and 3.

Example No. 16 (Comparative)

Additive free PELLETHANE 80A clone: Synthesis of a polyurethane formulation believed to be a clone of PELLETHANE 80A but not containing any anti-blocking agent (wax) or anti-oxidant.

Experimental Equipment: Tri-Pour beaker, Polyproylene stir bar, oven, and dry box.

Materials: POLYMEG 1000 (polytetramethylene glycol), MW 1000, from Quaker Oats Co., Butanediol from Aldrich, flaked Mondur M, (MDI) from Mobay Chemical, polymerization catalyst T-9 (stannous octoate) from Air Products.

Mixing/Polymerization Procedure: All processing was done in a dry box. In a Tri-Pour beaker 87.70 grams of POLYMEG 1000 and 10.60 grams of butanediol were blended. MDI was melted in a preheated 60° C. oven. The polyols were removed from the oven, one drop of catalyst T-9 was added and blended with the stir bar. The liquid MDI was added and the mixture stirred rapidly. There was a strong exothermic rise in temperature and viscosity built very rapidly. The liquid gelled in less than 30 seconds and gave a clear hard solid. The gelled polymer was post-cured at 115° C. for 16 hours.

Testing of Polymer: The dried polymer was compression molded into films at approximately 210° C. and annealed at 70° C. for 24 hours. All physical property testing was done according to the procedures described in Example No. 1. The results of that testing are presented in Tables 2 and 3.

Examples 17–20 (Comparatives)

Examples 17 to 20 demonstrate the properties of short C4 and C12 chain hard segments as a comparison to C20 and C111 hard segments.

Example No. 17 (Comparative)

One step solution polymerization of 1,10-Decanediol/MDI hard segment (42%) and PDMS diol soft segment (58%).

Experimental Equipment: The same as for Example No. 1.

Materials: Hard segment 1,10-decanediol, MW 174, from Aldrich Chemical Co. Inc. Diisocyanate, polymerization catalyst, PDMS diol, and solvents were the same as in Example No. 1.

Mixing Procedure: The mixing procedure was the same as in Example No. 1. The reactants were as follows: 6.41 grams of hard segment diol, 1,10-decanediol, 34.92 grams of PDMS diol, 63 grams of DMAC, 200 grams of distilled toluene, 19.48 grams of flaked MDI, and 50 ml of toluene. Total mixing time was 20 minutes.

Polymerization Procedure: The polymerization procedure was the same as in Example No. 1. The exothermic temperature rose from 93° C. to 103° C. After 13 minutes, the reaction temperature dropped to 90° C. and an FTIR scan showed no residual NCO peak at 2270 wave numbers. MDI (0.39 gram) was added to the reaction flask. After two minutes, the solution began to gel. The reaction was terminated by precipitation.

Precipitation Procedure: The precipitation procedure was the same as described in Example No. 1, except methanol was used instead of acetone. The polymer solids were dried in a vacuum oven at 50° C. overnight.

Testing of Polymers: The dried polymer was compression molded into films at approximately 190° C. and annealed at 80° C. for 24 hours. An FTIR scan showed no residual NCO peak. All physical property testing was done according to the procedures described in Example No. 1. The results of that testing are presented in Table 3.

Example No. 18 (Comparatives)

One step solution polymerization of 1,8-Octanediol/MDI hard segment (42%) and PDMS diol soft segment (58%).

Experimental equipment: The same as in Example No. 1.

Materials: Hard segment, 1,8-octanediol, MW 146, from Aldrich. Diiocyanate, polymerization catalyst, PDMS diol, and solvents were the same as in Example No. 1.

Mixing Procedure: The mixing procedure was the same as in Example No. 1. The reactants were as follows: 5.60 grams of hard segment 1,8-octane diol, 35.18 grams of soft segment PDMS diol, 63 grams of DMAC, 200 grams of toluene, 1959 grams of flaked MDI and 50 ml of toluene. Total mixing time was 21 minutes.

Polymerization Procedure: The polymerization procedure was the same as in Example No. 1. The exothermic temperature rose from 75° C. to 91° C. After 4 minutes, an FTIR scan showed no NCO peak, so 0.40 gram of MDI was added to the reaction flask. After 5 minutes, the viscosity was very high and the reaction was terminated by precipitation.

Precipitation Procedure: The precipitation procedure was the same as in Example No. 1 except methanol was used instead of acetone. The polymer solids were dried in a 50° C. vacuum oven.

Testing of Polymer: The dried polymer was compression molded into films at approximately 180° C. and annealed at 80° C. for 24 hours. An FTIR scan showed no NCO peak. All physical property testing was done according to the procedures described in Example No. 1. The results of that testing are presented in Table 3.

Example No. 19 (Comparative)

One step solution polymerization of 1,6-hexanediol/MDI hard segment (42%) and PDMS diol soft segment (58%).

Experimental Equipment: The same as for Example No. 1.

Materials: Hard segment 1,6-hexanediol, MW 118, from Aldrich. Soft segment PDMS diol, MDI, polymerization catalyst, and solvents were the same as in Example No. 1.

Mixing Procedure: The mixing procedure was the same as in Example No. 1. The reactants were as follows: 4.89 grams of 1,6-hexanediol, 35.12 grams of PDMS diol, 60 grams of DMAC, 160 grams of toluene, and 20.80 grams of flaked MDI. Total mixing time was 15 minutes.

Polymerization Procedure: The polymerization procedure was the same as in Example No. 1. The exothermic temperature rose from 75° C. to 92° C. After 8 minutes, the viscosity built rapidly and the solution started to gel. The reaction was terminated by precipitation.

Precipitation Procedure: The precipitation procedure was the same as described in Example No. 1 except methanol was used instead of acetone. The polymer solids were dried in a vacuum oven at 50° C. overnight.

Testing of Polymer: The dried polymer was compression molded into films at approximately 190° C. and annealed at 80° C. for 24 hours following the process described in Example No. 1. An FTIR scan on a 3 mil (0.008 cm) film showed a small NCO peak. All physical property testing was done according to the procedures described in Example No. 1. The results of that testing are presented in Table 3.

Example No. 20 (Comparative)

One step solution polymerization of 1,4-butanediol/MDI, hard segment (42%) and PDMS diol soft segment (58%).

Experimental Equipment: The same as for Example No. 1.

Materials: Hard segment 1,4-butanediol, MW 98, from Aldrich. Soft segment diol PDMS, diiocyanate, polymerization catalyst, and solvents were the same as in Example No. 1.

Mixing Procedure: The mixing procedure was the same as in Example No. 1. The reactants were as follows: 4.32 grams of 1,4-butanediol, 36.8 grams of PDMS diol, 60 grams of DMAC, 200 grams of toluene, 22.98 grams of flaked MDI, and 5 ml of toluene. Total mixing time was 30 minutes.

Polymerization Procedure: The polymerization procedure was the same as in Example No. 1. The exothermic temperature rose from 73° C. to 88° C. when one drop of polymerization catalyst T-9 was added to the flask. After 12 minutes, an FTIR scan showed a very small NCO peak. The reaction viscosity was very high and began to gel so the reaction was terminated by precipitation.

Precipitation Procedure: The precipitation procedure was the same as described in Example No. 1 except methanol was used instead of acetone. The polymer solids were dried in a vacuum oven at 50° C.

Testing of Polymer: The dried polymer was compression molded into films at approximately 200° C. and annealed at 80° C. for 24 hours following the process as outlined in Example No. 1. All physical property testing was done according to the procedures detailed in Example No. 1. The results of that testing are presented in Table 3.

Examples 21–23

Examples 21 to 23 compare the properties of formulations which contain only hard segments, no soft segments. They compare C12 to C20 and C176.

Example No. 21 (Comparative)

Neat polymerization of 1,12-dodecane diol/MDI hard segment 100%.

Experimental Equipment: Teflon beaker and a polypropylene stir stick.

Materials: Hard segment, 1,12-dodecanediol, from Aldrich, diisocyanate was MONDUR M (MDI) from Mobay Chemical.

Mixing/Polymerization Procedure: In dry box, the MDI, 1,12-dodecanediol, Teflon beaker and stir stick were preheated to 100° C. 1,12-Dodecanediol, 20.23 grams was added to the Telfon beaker, then 25.51 grams of liquid MDI were added. The contents were rapidly stirred making sure to wipe the bottom and sides of the beaker. After 15 seconds there was an exotherm and after 30 to 40 seconds the mixture gelled. The gelled mixture was post cured overnight in a 100° C. oven inside the dry box.

Testing of Polymer: The polymer was compression molded at 230° C. into films and annealed at 80° C. for 18 hours as per the procedure in Example No. 1. All physical property testing was done according to the procedures described in Example No. 1. The results of that testing are presented in Table 3.

Example No. 22

One step solution polymerization of LPE-314 Diol/MDI, hard segment 100%.

Experimental Equipment: The same as in Example No. 1.

Materials: Hard segment diol LPE-314, MW 314, MODUR M (MDI) from Mobay Chemical. Solvents, anhydrous DMAC, and anhydrous toluene from Aldrich Chemical Co. Catalyst T-9 (stannous octoate) from Air Products.

Mixing/Polymerization Procedure: In a dry box, 31.40 grams of LPE-314 diol was added to 60 grams of DMAC and 200 grams of toluene. The mixture was heated until the diol dissolved and the solution was clear at about 63° C. Flaked MDI, 25.61 grams, was added, slight exotherm to 66° C., two drops of polymerization catalyst T-9 were added. After two minutes the temperature rose to 73° C. and the solution became hazy. Upon heating the solution to 100° C. it cleared and started to build viscosity. An FTIR scan showed a medium NCO peak. LPE-314 diol, 0.63 gram, was added to the reactor. After 5 minutes, an FTIR scan showed a small NCO peak. The reaction was stopped by precipitation of the polymer solution. Total reaction time was 70 minutes.

Precipitation Procedure: The precipitation procedure was the same as in Example No. 1 except that methanol was used instead of acetone. The polymer solids were vacuum dried at 90° C. overnight.

Testing of Polymer: The dried polymer was compression molded into films at 1 90° C. and annealed according to the procedures described in Example No. 1. All physical property testing was done according to the procedures described in Example No. 1. The results of that testing are presented in Table 3.

Example No. 23

One step solution polymerization of LPE-2500 Diol/MDI, hard segment 100%.

Experimental Equipment: The same as in Example No. 1.

Materials: Hard segment diol LPE-2500, MW 2500, MONDUR M (MDI) from Mobay Chemical. Anhydrous toluene and catalyst T-9 (stannous octoate) from Air Products. Mixing/Polymerization Procedure: The mixing procedure was the same as outlined in Example No. 1. LPE-2500 diol, 34.92 grams, was added to 140 grams of toluene and heated to approximately 95° C. until the diol melted and the solution was clear. MDI, 3.57 grams, was added to the solution. After 15 minutes, two drops of polymerization catalyst T-9 was added to the solution. After 6 minutes, the solution had solidified so 50 ml of a 70/30 ratio of toluene to DMAC was added to solvate the polymer. The reaction mixture was heated to 104° C. after which the solution became clear but very viscous. An additional 50 ml of a 70/30 ratio of toluene to DMAC was added to lower the solution viscosity. The solution temperature fell to 91° C. and was reheated to 101° C. after which an additional 100 ml of toluene was added to lower the solution viscosity. An FTIR scan showed no NCO peak so 0.12 gram of MDI was added to the reaction. After 15 minutes, the reaction was terminated by precipitation. Total reaction time was 70 minutes.

Precipitation Procedure: The precipitation procedure was the same as described in Example No. 1.

Testing of the Polymer: The dried polymer was compression molded at 180° C. and annealed following the process described in Example No. 1. All physical property testing was done according to the procedures described in Example No. 1. The results of that testing are presented in Table 3.

Example No. 24

One step solution polymerization of LPE-314 Diol/MDI hard segment (50%) PTMEG-1000 diol soft segment (50%).

Experimental Equipment: The same as for example No. 1.

Materials: Hard segment diol was LPE-314 Diol, MW 314, MDI, soft segment diol PTMEG-1000, from Quaker Oats, polymerization catalyst T-9 (stannous octoate) from Air Products. Anhydrous DMAC and anhydrous toluene from Aldrich Chemical Co.

Mixing and Polymerization Procedure: The mixing procedure was the same as in Example No.1. LPE-314 diol, 12.48 grams, and PTMEG-1000, 30.04 grams, are added to 60 grams of DMAC and 200 grams of toluene. This was heated to 90° C. until a clear solution resulted and then 17.85 grams of MDI were added to the reactor after which there was a mild exotherm to 93° C. Two drops of polymerization catalyst T-9 were added to the reaction. The solution exothermed to 99° C. After 41 minutes, the reaction temperature returned to 90° C. and an FTIR scan, showed a medium NCO peak, so 0.71 gram of PTMEG diol and 0.22 gram of LPE-314 diol were added to the reaction. After an additional 58 minutes, 0.98 gram of PTMEG diol was added to the reaction. After 32 minutes, an FTIR scan showed a very small NCO peak. The reaction was terminated by precipitation. Total reaction time was 165 minutes.

Precipitation Procedure: The precipitation procedure was the same as in Example No. 1, except methanol was used instead of acetone. The polymer solids were vacuum dried at 50° C. overnight.

Testing of Polymer: The dried polymer was compression molded into films at 165° C. and annealed for 18 hours at 80° C. All physical property testing was done according to the procedures described in Example No. 1. The results of that testing are presented in Table 3.

Blocking Study

Objective: The following study tests the tendency of LPE based polyurethane elastomer to adhere (block) to themselves right after molding or extrusion before they have had a chance to develop their full crystallinity or before they have been annealed. This study compares LPE Diol containing polyurethane elastomers to commercial elastomers, some of which contain wax additives to prevent their blocking.

Materials: Example No. 9 (LPE-1596 Diol/MDI/PDMS containing polyurethane formulation), Example No.12 (LPE-314 Diol/MDI/PDMS containing polyurethane formulation), Example No. 15 (LPE-314 Diol/MDI/C36 branched diol (PRIPOL 2033), containing polyurethane formulation), PELLETHANE 80A, purchased from Dow Chemical, Example No. 16 (additive free "PELLETHANE-type" polyurethane formulation), and MDX 4-4516, commercial silicone elastomer purchased from Dow Coming.

Rationale: Polyurethane formulations redevelop their crystallinity after melt processing. This crystallinity can affect the blocking characteristics of the polyurethane formulation. The ability of LPE containing polyurethane formulations to more rapidly develop crystallinity than commercial polyurethanes is believed to result in less blocking tendencies. To test this hypothesis, all polyurethane samples were compression molded and tested immediately to represent real world extrusion and molding conditions. Note, pure PDMS silicone elastomers were included as a reference and were not tested immediately after molding since they do not develop crystallinity with time.

Sample Preparation & Testing: All polyurethane formulations were 25 mil (0.064 gram) films compression molded as per the procedure described in Example No. 1. Mold temperatures for the individual formulations were as follows. Example No. 9, mold temperature 185° C.; Example No. 12, mold temperature 190° C.; Example No. 16, mold temperature 215° C.; PELLETHANE 80A, mold temperature 215° C.; and Example No. 15, mold temperature 190° C. Immediately after molding, the films were quenched to room temperature and cut into one inch by two inch (5.1× 55.1 cm) lap shear shims. Two shims from each formulation were place on top of each other to give a 1 by 1 inch (2.5×2.5 cm) overlap tensile shear joint leaving a 1 by 1 inch (2.5×2.5 cm) tab on each end for gripping in the jaws of an INSTRON machine. Aluminum shims (0.064 inch or 0.16 cm long) were place one on the top, one on the bottom of the overlap joint and two small binder clips, one on each side of the test joint were used to hold the joint together and to apply pressure to the joint. Pressure was applied to the test joints for 18 hours after which the test joints were testing for their shear strength and the results reported as pound force needed to pull the two shims apart. The results of testing are presented in Tables 2 and 3.

TABLE 2

| Formulation | Composition | Blocking Force Results in Lbs |
|---|---|---|
| Example No. 9 | LPE-1596/MDI/PDMS | 4.9 lbs |
| Example No. 12 | LPE-314/MDI/PDMS | 2.5 lbs |
| Example No. 15 | LPE-314/MDI/C36 branched hydrocarbon Diol (PRIPOL-2033) | 4.6 lbs |
| Example No. 16 (Comparative) | POLYMEG 1000/BDO/MDI, no additives | 11.6 lb. |
| PELLETHANE 80A (Comparative) | Commercial polyurethane formulation, contains ant-blocking additive | 2.1 lbs |
| MDX 4-4516 (Comparative) | Commercial PDMS silicone elastomer | 5.2 lbs |

TABLE 3

Physical & Thermal Properties of Example Formulations

| Formulation | Composition | Ratio Hard to Soft Segment | Tensile Strength psi | Elongation % | Young's Modulus psi | Tear Strength ppi | Enthalpy (J/g) After Quench Cool |
|---|---|---|---|---|---|---|---|
| Example No. 1 | LPE-1520/MDI/PDMS | 42/58 | 1453 ± 122 | 522 ± 30 | 1775 ± 90 | 226 ± 13 | |
| Example No. 2 | LPE-1520/MDI/PTMEG-1000 | 42/58 | 2082 ± 71 | 743 ± 22 | 1940 ± 118 | 224 ± 6 | 55.8 |
| Example No. 3 | LPE-1520/MDI/Polyester-1820 (Adipate Glycol) | 42/58 | 2558 ± 59 | 779 ± 59 | 2520 ± 504 | 281 ± 45 | |
| Example No. 4 | LPE-1520/MDI/Polyester-1000 (Polycaprolactone) | 42/58 | 3434 ± 293 | 746 ± 22 | 2220 ± 216 | 306 ± 51 | |
| Example No. 5 | LPE-1520/MDI/Polyester-2000 (polycaprolactone) | 42/58 | 2047 ± 152 | 745 ± 41 | 2683 ± 263 | 275 ± 26 | |
| Example No. 6 | LPE-1520/MDI/PTMEG-650 | 42/58 | 1234 ± 72 | 826 ± 38 | 911 ± 75 | 209 ± 12 | |
| Example No. 7 | LPE-860/MDI/PDMS | 42/58 | 1330 ± 95 | 600 ± 33 | 2260 ± 73 | 290 ± 19 | |
| Example No. 8 (Comparative) | 1,4-butanediol/MDI/PDMS | 42/58 | 2578 ± 132 | 311 ± 18 | 8303 ± 279 | 580 ± 34 | |
| Example No. 9 | LPE-1596/MDI/PDMS | 42/58 | 1495 ± 122 | 481 ± 53 | 2440 ± 153 | 289 ± 8 | 39.3 |
| Example No. 10 (Comparative) | 1,12-dodecanediol/MDI/PDMS | 42/58 | 2841 ± 361 | 415 ± 27 | 7220 ± 258 | 554 ± 14 | 14.9 |
| Example No. 11 | LPE-314/MDI/PDMS | 42/58 | 2914 ± 97 | 465 ± 20 | 4627 ± 209 | 472 ± 21 | 22.1 |
| Example No. 12 | LPE-314/MDI/PDMS | 38/62 | 3020 ± 257 | 1237 ± 170 | 1983 ± 67 | 428 ± 11 | |
| Example No. 13 | LPE-620/MDI/PDMS | 40/60 | 2524 ± 110 | 571 ± 27 | 2628 ± 52 | 336 | |
| Example No. 14 | LPE-2026/MDI/DDI-1410/butanediol | 50/50 | 4078 ± 305 | 662 ± 28 | 18,375 ± 1724 | NA | 93 |
| Example No. 15 | LPE-314/MDI/C36 Diol (PRIPOL-2033) | 42/58 | 5188 ± 721 | 288 ± 16 | 33,407 ± 9134 | 952 ± 54 | 18.4 |
| Example No. 16 (Comparative) | 1,4-butanediol/MDI/PTMEG-1000 (additive free Pellethane 80A type formulation) | 42/58 | 6203 | 595 | 2993 | NA | |
| Example No. 17 (Comparative) | 1,10-decanediol/MDI/PDMS | 42/58 | 4010 ± 147 | 493 ± 18 | 5627 ± 345 | 561 ± 24 | 18.4 |
| Example No. 18 (Comparative) | 1,8-octanediol/MDI/PDMS | 42/58 | 3404 ± 59 | 507 ± 19 | 5101 ± 474 | 510 ± 69 | 17 |
| Example No. 19 (Comparative) | 1,6-hexanediol/MDI/PDMS | 42/58 | 3532 ± 305 | 484 ± 37 | 6145 ± 404 | 573 ± 19 | 11.4 |
| Example No. 20 (Comparative) | 1,4-butanediol/MDI/PDMS | 42/58 | 3286 ± 270 | 340 ± 33 | 7823 ± 56 | 610 ± 15 | 14.5 |
| Example No. 21 (Comparative) | 1,12-dodecanediol/MDI (no soft segment) | 100/0 | 8295 ± 198 | 50 ± 50 | 159,907 ± 44,052 | NA | 5.3 |
| Example No. 22 | LPE-314/MDI (no soft segment) | 100/0 | 6902 ± 730 | 239 ± 102 | 204,574 ± 19,666 | 1450 ± 116 | 62.4 |

TABLE 3-continued

Physical & Thermal Properties of Example Formulations

| Formulation | Composition | Ratio Hard to Soft Segment | Tensile Strength psi | Elongation % | Young's Modulus psi | Tear Strength ppi | Enthalpy (J/g) After Quench Cool |
|---|---|---|---|---|---|---|---|
| Example No. 23 | LPE-2500/MDI (no soft segment) | 100/0 | 3263 ± 160 | 455 | 46,268 ± 284 | NA | 127.3 |
| Example No. 24 | LPE-314/MDI/PTMEG-1000 | 50/50 | 4345 ± 525 | 487 ± 39 | 4914 ± 544 | 587 ± 40 | 30 |
| Pellethane 80 A (Comparative) | 1,4-butanediol/MDI/PTMEG-1000 | | | | | | 4.1 |

In-Vitro Oxidative Stability Study

Objective: To test various Linear Polyethylene Diols based polyurethane elastomer formulations in a strong oxidative solution to indicate potential resistance to oxidation if implanted in a human body, and to compare them to the present commercial standard.

Polymer sample compositions: Example No. 10—C12/MDI/PDMS; Example No. 12—C20/MDI/PDMS; Example No. 15—C20/MDI C36 Diol (PRIPOL-2033, Unichema, Chicago, Ill.); PELLETHANE 80A (Dow Chemical Co.).

Preparation of test solutions: (#1) 0.05M Cobalt Chloride hexahydrate with 10 weight percent hydrogen peroxide. To a 1 liter volumetric flask, 700 mls deionized water was added. It was placed on a magnetic stirrer plate and stirred with a magnetic stirrer bar, and then 200 mls of 50 weight percent hydrogen peroxide, from Aldrich was slowly added. Cobalt (11) chloride hexahydrate, from Aldrich, 11.90 grams, was then slowly added. It was stirred for 15 minutes before adding additional deionized water to bring total volume to 1000 mts. The resultant solution was pink in color and did not require filtration.

(#2) 0.05M Cobalt (11) acetylacetonate. To a 1 liter volumetric flask, 900 mls of deionized water was added. It was placed on a magnetic stirrer plate and stirred with a magnetic stirrer bar, and then 12.96 grams of cobalt acetylacetonate, from Aldrich was slowly added. It was then stirred for 3 hours before adding additional deionized water to bring the total volume to 1000 mls. The solution was filtered through a #40 Whatman filter paper using a Buchner funnel, water aspirator vacuum and suction flask to remove remaining solids resulting in a clear, dark,. reddish purple solution.

Preparation of polymer test samples: For each polymer composition, 25 mil films were compression molded at a temperature sufficiently above their melting point to produce a clear, bubble free film. With a type 5 die as described in ASTM D638, five dog bones were cut from each composition. Each dog bone sample was individually bent around a test fixture which consisted of a solid glass rod, 0.237 inch (0.6 cm) in diameter and 2.5 inches (6.4) long. Initially, each sample was held firmly in place around the glass rod with a small hemostat clamp. Each test specimen was tied in place using a length of 10 pound SPIDERWARE fishing line which was manufactured by Safariland and can be purchased at most local sporting goods stores. After five test specimens of the same polymer composition were tied around a test fixture, the excess tabs of each dog bone sample were cut off so that the test fixture would fit into an 8 ounce glass jar.

Test Procedure: Each completed test fixture with attached samples was placed into individual 8 ounce glass jars. One hundred milliliters of test solution #1 (Cobalt Chloride/Hydrogen Peroxide solution) was added into each jar. The jars with test specimens were stored in a 37° C. oven throughout the entire test sequence. Previous experimental data determined that the hydrogen peroxide in test solution #1 is decomposed in about 9 hours when stored at 37° C. Therefore, fresh test solution was used at the start and the end of Day 1 and Day 2 in order to maintain its maximum effectiveness.

At the start of day 3, test solution #1 was replaced with test solution #2, Cobalt acetylactonate (CoAcAc). Initially, test solution #2 was a dark reddish purple color due to the $Cobalt^{++}$ ion. Test solution #2 was used for the remaining test cycle.

With time at 37° C., the color of the CoAcAc test solution gradually changed to a dark brown color as the $Cobalt^{++}$ ion is converted to $Cobalt^{+++}$. When this was observed, the test solution was replaced with fresh CoAcAc. These changes were made on Days 5, 19, 35 and 49 days. At various intervals, samples were removed from their test solutions and rinsed in deionized water. Evaluations for the first 19 days were performed by visual observation using a lighted 1.75× magnifying glass. In order to better differentiate changes, starting with day 19, visual microscopic evaluations were recorded at 10× and Polaroid pictures were taken at 150×. Observations have been tabulated for 3 weeks and 6 weeks. The in-vitro test was terminated after eight weeks.

Discussion: Initial visual observations using a 1.75× lighted magnifying glass indicated that all polymers became stained but no degradation was detected until day 12. At this time, the PELLETHANE 80A sample had a pitted surface, but none of the surfaces of the other polymer compositions appeared to have been affected.

After 3 weeks, visual observations made with a 10× microscope found PELLETHANE 80A to have numerous cracks in its surface where it was bent around the glass rod fixture. These cracks were perpendicular to the applied stress and relieved any stress that was initially present. Between week 3 and week 6, these cracks became only slightly larger and did not cause the sample to rupture. None of the other test samples exhibited any surface cracking after 6 weeks. In addition, the surface of the PELLETHANE 80 A was dull and appeared to be eroded. The surfaces of the other sample compositions remained shiny in appearance. Visual results are summarized in Tables 4 and 5.

After 3 weeks, Polaroid pictures were taken at 150× to document any changes that were taking place at the microscopic level. The surface cracks on the PELLETHANE 80A surface were very apparent as well as its eroded surface.

TABLE 4

Summary of observations taken with 10 X microscope after 3 weeks.

|  | Ex. No. 10 C12/MDI/PDMS (Comparative) | Ex. No. 12 C20/MDI/PDMS | Ex. No. 15 C20/MDI/C 36 Diol | Control PELLETHANE E 80A |
|---|---|---|---|---|
| Film Clarity | Clear, transparent | Clear, transparent | Clear, transparent | Hazy, semi-transparent |
| Film Color | Golden brown | Golden brown | Greenish brown | Greenish brown |
| Surface Cracking | None | None | None | Yes, all around stressed area |

TABLE 5

Summary of observations taken with 10 X microscope after 6 weeks.

|  | Ex. No. 10 C12/MDI/PDMS (Comparative) | Ex. No. 12 C20/MDI/PDMS | Ex. No. 15 C20/MDI/C 36 Diol | Control PELLETHANE E 80A |
|---|---|---|---|---|
| Visual Film Clarity | Clear, transparent | Clear, transparent | Clear, transparent | Dull, semi-transparent |
| Visual Film Color | Golden brown | Golden brown | Greenish brown | Greenish yellow |
| Surface cracking | None | None | None | Multiple cracks in polymer surface in stressed area |

X-Ray Diffraction Study

Objective: To compare the crystalline character of the LPE diol containing polyurethane formulations, LPE-314 Diol, and LPE-1596 Diol, to the polyurethane formulations containing 1,12-dodencanediol, and commercial Pellethane 80A, with High Density Polyethylene (HDPE).

Test Samples: Wide Angle Diffraction Patterns were run on the following samples. Example No.11 (LPE-314/MDI/PDMS), Example No.9 (LPE-1596/MDI/PDMS), Example No.12 (1,12-dodecanediol/MDI/PDMS), PELLETHANE 80A (Dow Chemical Co.), and HDPE a variable under the product designation P5002-00 (Quantum Chemical Corp., Cincinnati, Ohio).

Testing Procedure: Samples were run on a Philips X'Pert-MPD X-ray Diffractometer. An approximately 1.5 cm×1.5 cm flat sample was mounted and measured under the following parameters: set time of 2 or 10 seconds, 2θ=5 to 60 degrees, 30 kV, 20 mA.

Test Results and Discussion: The diffraction pattern of Example No. 9 (FIG. 2) showed a pattern which is characteristic of the HDPE diffraction pattern with both major peak at about 21.5 and 23.5. In addition the diffraction pattern for Example No. 9 showed a peak at about 18.5, believed to be attributable to polyurethane character. The diffraction pattern of Example No. 11 (FIG. 3) showed a pattern which has a shoulder at about 21.5, believed to be attributable to HDPE character. This peak was not as large as the peak in Example No. 9 because the lower molecular weight of the LPE-314 Diol, 314 grams per mole, versus the LPE-1596 Diol, 1596 grams per mole, resulted in less hydrocarbon in the formulation on a weight bases and therefore a lower percentage of polyethylene character. In addition, it is believed that the methylene chain length of this diol, 20 $CH_2$ units, is long enough to organize as polyethylene crystallites and therefore polyurethane formulation containing this diol will have some polyethylene character as well as polyurethane character, reference the peak at about 18.5.

Figure 5:
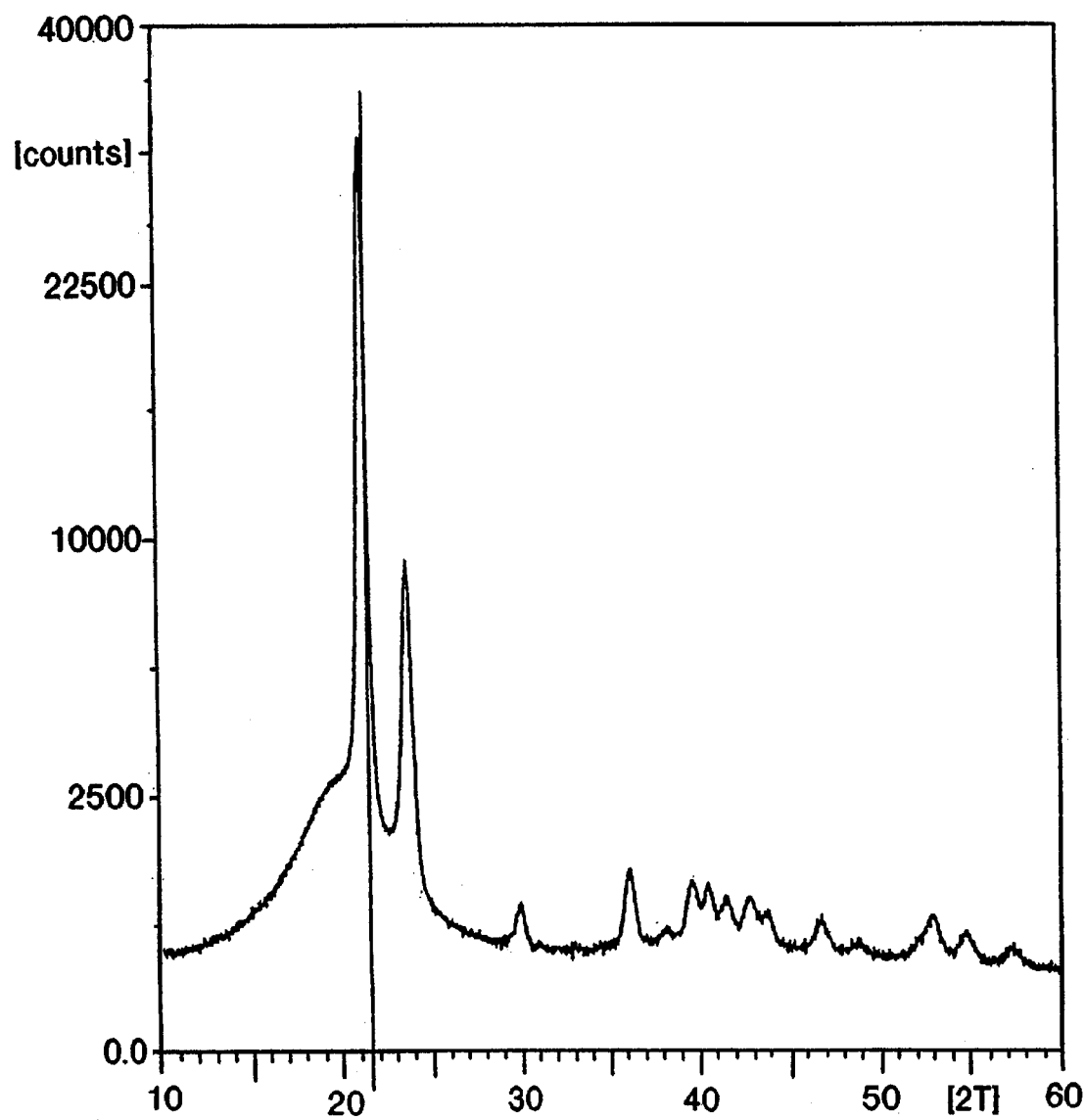
FIG. 5 is a comparative X-ray Diffraction Pattern of a high density polyethylene showing crystallinity of only polyethylene character.
Figure 6:
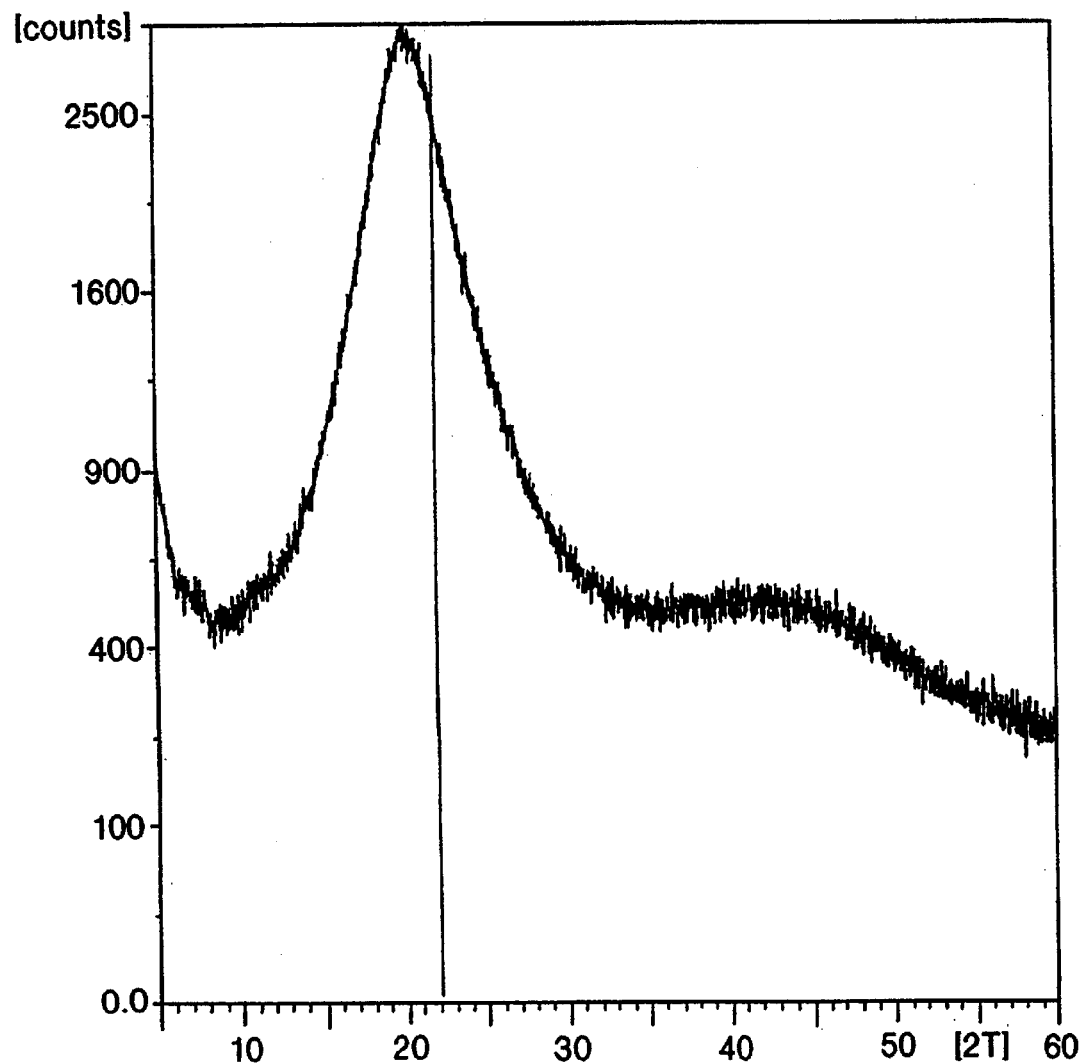
FIG. 6 is a comparative X-ray Diffraction Pattern of a polyurethane polymer obtained under the trade designation PELLETHANE from Dow Chemical Co. showing crystallinity of only polyurethane character.

For comparison purposes, the diffraction pattern of Example No. 12 (FIG. 4) showed a peak at 18.5 which is associated with the polyurethane character but no apparent peak or shoulder at about 21.5. It is believed that this formulation does not contain polyethylene character due to the shorter methylene chain length (12 carbons), which is apparently not long enough to organize as polyethylene in a polyurethane formulation. The diffraction pattern of a high density polyethylene obtained from Quantum Chemical Corp. is shown in FIG. 5. The diffraction pattern of a polyurethane obtained under the trade designation PELLETHANE 80A from Dow Chemical Co. (FIG. 6) showed no peak at about 21.5, which would indicate polyethylene character, but does have a polyurethane peak at about 18.5. This peak is the same as for the other polyurethane formulations.

The complete disclosure of all patents, patent documents, and publications cited herein are incorporated by reference, as if individually incorporated. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A medical device comprising a biomaterial formed from a segmented polymer comprising urethane groups and saturated linear polyethylene moities having greater than 12 carbon atoms per moiety.

2. The medical device of claim 1 wherein the polymer comprises at least about 30 weight percent saturated linear polyethylene moieties having greater than 12 carbon atoms per moiety, based on the total weight of the polymer.

3. The medical device of claim 2 wherein the polymer comprises at least about 30 weight percent saturated linear polyethylene moieties having at least about 20 carbon atoms per moiety, based on the total weight of the polymer.

4. The medical device of claim 2 wherein the polymer is prepared from isocyanate-containing compounds and saturated linear polyethylene diols having the formula HO—(—$CH_2$—)$_n$—OH wherein n is at least about 20.

5. The medical device of claim 4 wherein n is at least about 35.

6. The medical device of claim 4 wherein n is no greater than about 45.

7. The medical device of claim 1 wherein the polymer has a molecular weight of greater than about 500.

8. The medical device of claim 1 wherein the polymer is free of sufur- or phosphorus-containing groups.

9. The medical device of claim 1 wherein the polymer comprises phase separated hard and soft segments, wherein the hard segments comprise the saturated linear polyethylene moieties having greater than 12 carbon atoms per moiety.

10. The medical device of claim 9 wherein the soft segments comprise silicone groups.

11. A medical device comprising a biomaterial formed from a segmented polymer consisting essentially of alternating urethane groups and saturated linear polyethylene moieties having greater than 12 carbon atoms per moiety.

12. A medical device comprising a biomaterial formed from a segmented polymer comprising urethane groups and saturated linear polyethylene moities having greater than 12 carbon atoms per unit, wherein the polymer has an elongation of greater than 50%.

13. A medical electrical lead comprising:
   (a) an elongated insulation sheath biomaterial formed from a segmented polymer comprising urethane groups and saturated linear polyethylene moieties having greater than 12 carbon atoms per moiety;
   (b) an elongated conductor, located within the elongated insulation sheath;
   (c) an electrode coupled to a distal end of the elongated conductor; and
   (d) an electrical connector coupled to a proximal end of the elongated conductor.

14. The medical electrical lead of claim 13 wherein the polymer comprises at least about 30 weight percent saturated linear polyethylene moieties having greater than 12 carbon atoms per moiety, based on the total weight of the polymer.

15. The medical electrical lead of claim 14 wherein the polymer comprises at least about 30 weight percent saturated linear polyethylene moieties having at least about 20 carbon atoms per moiety, based on the total weight of the polymer.

16. The medical electrical lead of claim 14 wherein the polymer is prepared from isocyanate-containing compounds and saturated linear polyethylene diols having the formula HO—(—CH$_2$—)$_n$—OH wherein n is at least about 20.

17. The medical electrical lead of claim 16 wherein n is at least about 35.

18. The medical electrical lead of claim 17 wherein n is no greater than about 45.

19. The medical electrical lead of claim 13 wherein the polymer has a molecular weight of greater than about 500.

20. The medical electrical lead of claim 13 wherein the polymer is free of sufur- or phosphorus-containing groups.

21. The medical electrical lead of claim 13 wherein the polymer comprises phase separated hard and soft segments, wherein the hard segments comprise the saturated linear polyethylene moieties having greater than 12 carbon atoms per moiety.

22. The medical electrical lead of claim 21 wherein the soft segments comprise silicone groups.

23. A medical device comprising a biomaterial formed from a segmented polymer comprising urethane groups, wherein the polymer is prepared from isocyanate-containing compounds and compounds of the formula:

wherein n>12.

24. The medical device of claim 23 wherein n is at least about 20.

25. The medical device of claim 24 wherein n is at least about 35.

26. The medical device of claim 24 wherein n is no greater than about 45.

27. The medical device of claim 23 wherein the polymer comprises phase separated hard and soft segments, wherein the hard segments comprise the saturated linear polyethylene moieties having greater than 12 carbon atoms per moiety.

28. The medical device of claim 27 wherein the soft segments comprise silicone groups.

29. A method of using a medical electrical lead, the method comprising:
   providing a medical electrical lead comprising an elongated insulation sheath biomaterial formed from a segmented polymer comprising urethane and saturated linear polyethylene units having greater than 12 carbon atoms per moiety;
   electrically connecting a first end of the medical electrical lead to implantable medical device; and
   electrically stimulating or sensing a second end of the lead.

* * * * *